United States Patent
Defosset et al.

(10) Patent No.: US 11,510,723 B2
(45) Date of Patent: Nov. 29, 2022

(54) TUMOR ABLATION DEVICE AND RELATED SYSTEMS AND METHODS

(71) Applicant: DFine, Inc., South Jordan, UT (US)

(72) Inventors: Joshua Defosset, Los Gatos, CA (US); Nate Shirley, Pleasant Grove, UT (US); Eric Wong, Sunnyvale, CA (US); Craig Purdy, Sunnyvale, CA (US); Oleg Yurchak, Milpitas, CA (US); Jimmy Chi-Yun Chan, San Mateo, CA (US)

(73) Assignee: DFine, Inc., South Jordan, UT (US)

( * ) Notice: Subject to any disclaimer, the term of this patent is extended or adjusted under 35 U.S.C. 154(b) by 362 days.

(21) Appl. No.: 16/677,216

(22) Filed: Nov. 7, 2019

(65) Prior Publication Data
US 2020/0146744 A1   May 14, 2020

Related U.S. Application Data

(60) Provisional application No. 62/757,578, filed on Nov. 8, 2018, provisional application No. 62/757,596, filed on Nov. 8, 2018.

(51) Int. Cl.
*A61B 18/14* (2006.01)
*A61B 18/12* (2006.01)
(Continued)

(52) U.S. Cl.
CPC .......... *A61B 18/14* (2013.01); *A61B 18/1206* (2013.01); *G06F 3/0482* (2013.01);
(Continued)

(58) Field of Classification Search
CPC ................ A61B 18/1206; A61B 18/14; A61B 2017/00057; A61B 2017/00115;
(Continued)

(56) References Cited

U.S. PATENT DOCUMENTS

| 2,688,329 A | 9/1954 | Wallace |
| 3,140,623 A | 7/1964 | Hoose |

(Continued)

FOREIGN PATENT DOCUMENTS

| CA | 2785207 | 7/2011 |
| CN | 88203061 | 11/1988 |

(Continued)

OTHER PUBLICATIONS

US 7,063,700 B2, 06/2006, Michelson (withdrawn)
(Continued)

*Primary Examiner* — Michael F Peffley
(74) *Attorney, Agent, or Firm* — Dorsey & Whitney LLP

(57) ABSTRACT

Tumor ablation devices and related systems and methods are disclosed. Some tumor ablation devices include an RF energy delivery probe with two conductors and one or more thermocouples. The thermocouple measures a temperature at a location on one of the conductors. A generator can produce a current to be conducted between the first conductor and the second conductor via tissue within a desired ablation region. The ablation regions created by the RF energy delivery probe are symmetric about poles of the first conductor and the second conductor. A distal portion of the RF energy delivery probe may articulate, enabling a user to position the RF energy delivery probe in a proper position to ablate the tumor. The thermocouples may be disposed on a flexible or wired thermocouple circuit that is disposed between insulators.

19 Claims, 10 Drawing Sheets

(51) Int. Cl.
*G06F 3/0482* (2013.01)
*G06F 3/0488* (2022.01)
*A61B 18/00* (2006.01)
*A61B 17/00* (2006.01)
*A61B 90/00* (2016.01)

(52) U.S. Cl.
CPC .. *G06F 3/0488* (2013.01); *A61B 2017/00057* (2013.01); *A61B 2017/0088* (2013.01); *A61B 2017/00115* (2013.01); *A61B 2017/00212* (2013.01); *A61B 2017/00393* (2013.01); *A61B 2018/0072* (2013.01); *A61B 2018/00339* (2013.01); *A61B 2018/00577* (2013.01); *A61B 2018/00821* (2013.01); *A61B 2018/00875* (2013.01); *A61B 2018/00916* (2013.01); *A61B 2090/376* (2016.02)

(58) Field of Classification Search
CPC ........... A61B 2017/00212; A61B 2017/00393; A61B 2017/0088; A61B 2018/00339; A61B 2018/00577; A61B 2018/00702; A61B 2018/0072; A61B 2018/00791; A61B 2018/00821; A61B 2018/00875; A61B 2018/00916; A61B 2090/376; G06F 2/0482; G06F 2/04847; G06F 2/0488
See application file for complete search history.

(56) References Cited

U.S. PATENT DOCUMENTS

| | | | |
|---|---|---|---|
| 3,228,400 A | 1/1966 | Armao | |
| 3,503,385 A | 3/1970 | Stevens | |
| 3,625,200 A | 12/1971 | Muller | |
| 3,664,344 A | 5/1972 | Bryne | |
| 3,794,039 A | 2/1974 | Kollner et al. | |
| 3,908,637 A | 9/1975 | Doroshow | |
| 4,033,331 A | 7/1977 | Guss et al. | |
| 4,131,597 A | 12/1978 | Bluethgen et al. | |
| 4,236,520 A | 12/1980 | Anderson | |
| 4,276,880 A | 7/1981 | Malmin | |
| 4,294,251 A | 10/1981 | Grennwald et al. | |
| 4,337,773 A | 7/1982 | Raftopoulos et al. | |
| 4,386,717 A | 6/1983 | Koob | |
| 4,399,814 A | 8/1983 | Pratt, Jr. et al. | |
| 4,411,266 A | 10/1983 | Cosman | |
| 4,456,017 A | 6/1984 | Miles | |
| 4,473,077 A | 9/1984 | Noiles | |
| 4,476,861 A | 10/1984 | Dimakos et al. | |
| 4,578,061 A | 3/1986 | Lemelson | |
| 4,586,923 A | 5/1986 | Gould et al. | |
| 4,595,006 A | 6/1986 | Burke et al. | |
| 4,619,263 A | 10/1986 | Frisbie et al. | |
| 4,627,434 A | 12/1986 | Murray | |
| 4,641,654 A | 2/1987 | Samson et al. | |
| 4,653,489 A | 3/1987 | Tronzo | |
| 4,668,295 A | 5/1987 | Bajpai | |
| 4,682,596 A * | 7/1987 | Bales ................ | A61B 18/1492 606/39 |
| 4,719,968 A | 1/1988 | Speros | |
| 4,722,948 A | 2/1988 | Sanderson | |
| 4,731,054 A | 3/1988 | Billeter et al. | |
| 4,742,817 A | 5/1988 | Kawashima et al. | |
| 4,747,840 A | 5/1988 | Ladika et al. | |
| 4,748,969 A | 6/1988 | Wardle | |
| 4,784,638 A | 11/1988 | Ghajar et al. | |
| 4,795,602 A | 1/1989 | Pretchel et al. | |
| 4,842,603 A | 6/1989 | Draenert | |
| 4,843,112 A | 6/1989 | Gerhart et al. | |
| 4,846,814 A | 7/1989 | Ruiz | |
| 4,865,586 A | 9/1989 | Hedberg | |
| 4,869,906 A | 9/1989 | Dingeldein et al. | |
| 4,888,366 A | 12/1989 | Chu et al. | |
| 4,900,303 A | 2/1990 | Lemelson | |
| 4,961,730 A | 10/1990 | Bodicky et al. | |
| 4,961,731 A | 10/1990 | Poncy | |
| 4,963,151 A | 10/1990 | Ducheyene et al. | |
| 4,969,870 A | 11/1990 | Kramer et al. | |
| 4,969,888 A | 11/1990 | Scholten et al. | |
| 4,982,730 A | 1/1991 | Royce | |
| 4,998,923 A | 3/1991 | Samson et al. | |
| 5,004,501 A | 4/1991 | Faccioli | |
| 5,017,627 A | 5/1991 | Bonfield | |
| 5,046,513 A | 9/1991 | O'Leary et al. | |
| 5,049,137 A | 9/1991 | Thompson | |
| 5,049,157 A | 9/1991 | Mittelmeier et al. | |
| 5,059,193 A | 10/1991 | Kuslich | |
| 5,085,659 A * | 2/1992 | Rydell ................ | A61B 10/04 606/170 |
| 5,085,861 A | 2/1992 | Gerhart et al. | |
| 5,088,991 A | 2/1992 | Weldon | |
| 5,116,305 A | 2/1992 | Milder et al. | |
| 5,092,891 A | 3/1992 | Kummer et al. | |
| 5,103,804 A | 4/1992 | Abele | |
| 5,108,404 A | 4/1992 | Scholten et al. | |
| 5,112,303 A | 5/1992 | Pudenz et al. | |
| 5,114,414 A | 5/1992 | Buchbinder | |
| 5,147,334 A | 9/1992 | Moss | |
| 5,156,606 A | 10/1992 | Chin | |
| 5,163,431 A | 11/1992 | Greip | |
| 5,184,757 A | 2/1993 | Giannuzzi | |
| 5,188,619 A | 2/1993 | Myers | |
| 5,196,201 A | 3/1993 | Larsson et al. | |
| 5,197,971 A | 3/1993 | Bonutti | |
| 5,211,631 A | 5/1993 | Sheaff | |
| 5,231,989 A | 8/1993 | Middleman et al. | |
| 5,242,082 A | 9/1993 | Giannuzzi | |
| 5,264,214 A | 11/1993 | Rhee et al. | |
| 5,266,248 A | 11/1993 | Ohtsuka et al. | |
| 5,269,750 A | 12/1993 | Grulke et al. | |
| 5,282,821 A | 2/1994 | Donahue | |
| 5,284,128 A | 2/1994 | Hart | |
| 5,285,795 A | 2/1994 | Ryan et al. | |
| 5,295,980 A | 3/1994 | Ersek | |
| 5,296,026 A | 3/1994 | Monroe et al. | |
| 5,308,342 A | 5/1994 | Sepetka et al. | |
| 5,322,064 A | 6/1994 | Lundquist | |
| 5,322,505 A | 6/1994 | Krause et al. | |
| 5,334,181 A | 8/1994 | Rubinsky et al. | |
| 5,336,699 A | 8/1994 | Cooke et al. | |
| 5,342,356 A * | 8/1994 | Ellman ................ | A61B 18/14 606/32 |
| 5,343,877 A | 9/1994 | Park | |
| 5,352,715 A | 10/1994 | Wallace et al. | |
| 5,356,629 A | 10/1994 | Sander | |
| 5,360,416 A | 11/1994 | Ausherman et al. | |
| 5,368,598 A | 11/1994 | Hasson | |
| 5,372,587 A | 12/1994 | Hammerslag et al. | |
| 5,378,234 A | 1/1995 | Hammerslag et al. | |
| 5,380,307 A | 1/1995 | Chee et al. | |
| 5,385,563 A | 1/1995 | Gross | |
| 5,389,073 A | 2/1995 | Imran | |
| 5,425,770 A | 6/1995 | Piez et al. | |
| 5,431,168 A | 7/1995 | Webster, Jr. | |
| 5,431,639 A | 7/1995 | Shaw | |
| 5,437,636 A | 8/1995 | Snoke et al. | |
| 5,449,301 A | 9/1995 | Hanna et al. | |
| 5,449,351 A | 9/1995 | Zohmann | |
| 5,458,597 A | 10/1995 | Edwards et al. | |
| 5,480,382 A | 1/1996 | Hammerslag et al. | |
| 5,484,424 A | 1/1996 | Cottenceau et al. | |
| 5,489,275 A | 2/1996 | Thompson et al. | |
| 5,496,330 A | 3/1996 | Bates et al. | |
| 5,512,610 A | 4/1996 | Lin | |
| 5,514,130 A | 5/1996 | Baker | |
| 5,514,137 A | 5/1996 | Coutts | |
| 5,531,715 A | 7/1996 | Engelson et al. | |
| 5,535,922 A | 7/1996 | Maziarz | |
| 5,549,542 A | 8/1996 | Kovalcheck | |
| 5,549,637 A | 8/1996 | Crainich | |
| 5,549,679 A | 8/1996 | Kuslich | |
| 5,554,114 A | 9/1996 | Wallace et al. | |

(56) References Cited

U.S. PATENT DOCUMENTS

| | | |
|---|---|---|
| 5,571,085 A | 11/1996 | Accisano, III |
| 5,571,088 A | 11/1996 | Lennox |
| 5,574,075 A | 11/1996 | Draemert |
| 5,599,346 A | 2/1997 | Edwards et al. |
| 5,616,121 A | 4/1997 | McKay |
| 5,620,447 A | 4/1997 | Smith et al. |
| 5,620,467 A | 4/1997 | Wagner |
| 5,624,396 A | 4/1997 | McNamara et al. |
| 5,628,771 A | 5/1997 | Mizukawa et al. |
| 5,637,090 A | 6/1997 | McGee |
| 5,637,091 A | 6/1997 | Hakky et al. |
| 5,662,680 A | 9/1997 | Desai |
| 5,681,282 A | 10/1997 | Eggers et al. |
| 5,681,289 A | 10/1997 | Wilcox et al. |
| 5,681,317 A | 10/1997 | Caldarise |
| 5,685,826 A | 11/1997 | Bonutti |
| 5,695,513 A | 12/1997 | Johnson et al. |
| 5,697,281 A | 12/1997 | Eggers et al. |
| 5,697,536 A | 12/1997 | Eggers et al. |
| 5,697,909 A | 12/1997 | Eggers et al. |
| 5,700,157 A | 12/1997 | Chung |
| 5,704,926 A | 1/1998 | Sutton |
| 5,709,697 A | 1/1998 | Ratcliff et al. |
| 5,725,568 A | 3/1998 | Hastings |
| 5,735,829 A | 4/1998 | Cherian |
| 5,741,320 A | 4/1998 | Thornton et al. |
| 5,766,153 A | 6/1998 | Eggers et al. |
| 5,800,408 A | 9/1998 | Strauss et al. |
| 5,810,804 A | 9/1998 | Gough |
| 5,810,867 A | 9/1998 | Zarbateny et al. |
| 5,820,592 A | 10/1998 | Hammerslag et al. |
| 5,833,632 A | 11/1998 | Jacobsen et al. |
| 5,833,692 A | 11/1998 | Cesarini et al. |
| 5,847,046 A | 12/1998 | Jiang et al. |
| 5,849,028 A | 12/1998 | Chen |
| 5,851,212 A | 12/1998 | Zirps et al. |
| 5,855,577 A | 1/1999 | Murphy-Chutorian et al. |
| 5,858,003 A | 1/1999 | Atala |
| 5,860,952 A | 1/1999 | Quinn |
| 5,860,974 A | 1/1999 | Abele |
| 5,876,373 A | 3/1999 | Giba et al. |
| 5,891,027 A | 4/1999 | Tu |
| 5,902,251 A | 5/1999 | Vanhooydonk |
| 5,902,839 A | 5/1999 | Lautenschlager et al. |
| 5,914,356 A | 6/1999 | Erbe |
| 5,921,956 A | 7/1999 | Grinberg et al. |
| 5,928,239 A | 7/1999 | Mirza |
| 5,931,829 A | 8/1999 | Burbank et al. |
| 5,944,715 A | 8/1999 | Goble et al. |
| 5,947,964 A | 9/1999 | Eggers |
| 5,972,015 A | 10/1999 | Scribner et al. |
| 5,997,581 A | 12/1999 | Khalili |
| 6,019,765 A | 2/2000 | Thornhill et al. |
| 6,027,487 A | 2/2000 | Crocker |
| 6,030,360 A | 2/2000 | Biggs |
| 6,048,346 A | 4/2000 | Reiley et al. |
| 6,059,739 A | 5/2000 | Baumann |
| 6,063,078 A | 5/2000 | Wittkampf |
| 6,064,902 A | 5/2000 | Haissaguerre |
| 6,066,154 A | 5/2000 | Reiley et al. |
| 6,066,176 A | 5/2000 | Oshida |
| 6,073,051 A | 6/2000 | Sharkey et al. |
| 6,080,801 A | 6/2000 | Draenert et al. |
| 6,099,514 A | 8/2000 | Sharkey et al. |
| 6,106,524 A * | 8/2000 | Eggers .............. A61B 5/0531 606/41 |
| 6,106,539 A | 8/2000 | Fortier |
| 6,110,155 A | 8/2000 | Baudino |
| 6,123,702 A | 9/2000 | Swanson |
| 6,127,597 A | 10/2000 | Beyar et al. |
| 6,135,999 A | 10/2000 | Fanton et al. |
| 6,146,355 A | 11/2000 | Biggs |
| 6,156,254 A | 12/2000 | Andrews et al. |
| 6,183,435 B1 | 2/2001 | Bumbalough et al. |
| 6,203,507 B1 | 3/2001 | Wadsworth et al. |
| 6,203,574 B1 | 3/2001 | Kawamura |
| 6,228,052 B1 | 5/2001 | Pohndorf |
| 6,228,904 B1 | 5/2001 | Yadav et al. |
| 6,231,569 B1 | 5/2001 | Bek et al. |
| 6,231,615 B1 | 5/2001 | Preissman |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,251,092 B1 | 6/2001 | Qin et al. |
| 6,258,086 B1 | 7/2001 | Ashley et al. |
| 6,270,476 B1 | 8/2001 | Santoianni et al. |
| 6,280,413 B1 | 8/2001 | Clark et al. |
| 6,280,434 B1 | 8/2001 | Kinoshita et al. |
| 6,280,441 B1 | 8/2001 | Ryan |
| 6,280,456 B1 | 8/2001 | Scribner et al. |
| 6,280,473 B1 | 8/2001 | Lemperle et al. |
| 6,283,960 B1 | 9/2001 | Ashley |
| 6,291,547 B1 | 9/2001 | Lyles |
| 6,312,428 B1 | 11/2001 | Eggers |
| 6,312,454 B1 | 11/2001 | Stockel et al. |
| 6,332,894 B1 | 12/2001 | Stalcup et al. |
| 6,348,055 B1 | 2/2002 | Preissman |
| 6,352,533 B1 | 3/2002 | Ellman et al. |
| 6,358,251 B1 | 3/2002 | Mirza |
| 6,375,659 B1 | 4/2002 | Erbe et al. |
| 6,383,188 B2 | 5/2002 | Kuslich et al. |
| 6,383,190 B1 | 5/2002 | Preissman |
| 6,395,007 B1 | 5/2002 | Bhatnagar et al. |
| 6,408,889 B1 | 6/2002 | Komachi |
| 6,409,722 B1 | 6/2002 | Hoey et al. |
| 6,428,894 B1 | 8/2002 | Babich et al. |
| 6,437,019 B1 | 8/2002 | Rusin et al. |
| 6,440,138 B1 | 8/2002 | Reiley et al. |
| 6,447,506 B1 | 9/2002 | Swanson et al. |
| 6,447,514 B1 | 9/2002 | Stalcup et al. |
| 6,464,683 B1 | 10/2002 | Samuelson et al. |
| 6,478,793 B1 | 11/2002 | Cosman et al. |
| 6,479,565 B1 | 11/2002 | Stanley |
| 6,484,904 B1 | 11/2002 | Horner et al. |
| 6,506,217 B1 | 1/2003 | Arnett |
| 6,511,471 B2 | 1/2003 | Rosenman et al. |
| 6,524,296 B1 | 2/2003 | Beals |
| 6,565,588 B1 | 5/2003 | Clement et al. |
| 6,575,969 B1 | 6/2003 | Rittman et al. |
| 6,575,978 B2 | 6/2003 | Peterson et al. |
| 6,576,249 B1 | 6/2003 | Gendler et al. |
| 6,582,446 B1 | 6/2003 | Marchosky |
| 6,592,559 B1 | 7/2003 | Pakter et al. |
| 6,599,961 B1 | 7/2003 | Pienkowski et al. |
| 6,602,248 B1 | 8/2003 | Sharps et al. |
| 6,607,544 B1 | 8/2003 | Boucher et al. |
| 6,613,054 B2 | 9/2003 | Scribner et al. |
| 6,620,162 B2 | 9/2003 | Kuslich et al. |
| 6,622,731 B2 | 9/2003 | Daniel et al. |
| 6,623,448 B2 | 9/2003 | Slater |
| 6,638,268 B2 | 10/2003 | Naizi |
| 6,663,647 B2 | 10/2003 | Reiley et al. |
| 6,641,587 B2 | 11/2003 | Scribner et al. |
| 6,645,213 B2 | 11/2003 | Sand et al. |
| 6,676,665 B2 | 1/2004 | Foley et al. |
| 6,679,886 B2 | 1/2004 | Weikel et al. |
| 6,689,823 B1 | 2/2004 | Bellare et al. |
| 6,692,532 B1 | 2/2004 | Healy et al. |
| 6,716,216 B1 | 4/2004 | Boucher et al. |
| 6,719,761 B1 | 4/2004 | Reiley et al. |
| 6,719,773 B1 | 4/2004 | Boucher et al. |
| 6,726,691 B2 | 4/2004 | Osorio et al. |
| 6,730,095 B2 | 5/2004 | Olson, Jr. et al. |
| 6,740,090 B1 | 5/2004 | Cragg et al. |
| 6,740,093 B2 | 5/2004 | Hochschuler et al. |
| 6,743,239 B1 | 6/2004 | Kuehn et al. |
| 6,746,451 B2 | 6/2004 | Middleton et al. |
| 6,752,863 B2 | 6/2004 | Lyles et al. |
| 6,753,007 B2 | 6/2004 | Haggard et al. |
| 6,770,079 B2 | 8/2004 | Bhatnagar et al. |
| 6,814,734 B2 | 11/2004 | Chappuis et al. |
| 6,814,736 B2 | 11/2004 | Reiley et al. |
| 6,818,001 B2 | 11/2004 | Wulfman et al. |
| 6,832,984 B2 | 12/2004 | Stelzer et al. |

(56) References Cited

U.S. PATENT DOCUMENTS

| | | | |
|---|---|---|---|
| 6,835,193 B2 | 12/2004 | Epstein et al. | |
| 6,837,867 B2 | 1/2005 | Kortelling | |
| 6,863,672 B2 | 3/2005 | Reiley et al. | |
| 6,869,430 B2 | 3/2005 | Balbierz et al. | |
| 6,869,445 B1 | 3/2005 | Johnson | |
| 6,875,219 B2 | 4/2005 | Arramon | |
| 6,881,214 B2 * | 4/2005 | Cosman | A61B 18/1477 606/45 |
| 6,887,246 B2 | 5/2005 | Bhatnagar et al. | |
| 6,899,715 B1 | 5/2005 | Beaty | |
| 6,899,719 B2 | 5/2005 | Reiley et al. | |
| 6,907,884 B2 | 6/2005 | Pellegrino et al. | |
| 6,913,594 B2 | 7/2005 | Coleman et al. | |
| 6,916,306 B1 | 7/2005 | Jenkins et al. | |
| 6,923,813 B2 | 8/2005 | Phillips | |
| 6,945,956 B2 | 9/2005 | Waldhauser et al. | |
| 6,953,594 B2 | 10/2005 | Lee et al. | |
| 6,955,716 B2 | 10/2005 | Xu et al. | |
| 6,976,987 B2 | 12/2005 | Flores | |
| 6,979,312 B2 | 12/2005 | Shimada | |
| 6,979,352 B2 | 12/2005 | Reynolds | |
| 6,981,981 B2 | 1/2006 | Reiley et al. | |
| 6,991,616 B2 | 1/2006 | Bencini et al. | |
| 6,998,128 B2 | 2/2006 | Haggard et al. | |
| 7,004,930 B2 | 2/2006 | Marshall | |
| 7,004,945 B2 | 3/2006 | Boyd et al. | |
| 7,008,433 B2 | 3/2006 | Voellmicke et al. | |
| 7,018,460 B2 | 3/2006 | Xu et al. | |
| 7,022,133 B2 | 4/2006 | Yee et al. | |
| 7,029,468 B2 | 4/2006 | Honebrink | |
| 7,044,954 B2 | 5/2006 | Reiley et al. | |
| 7,059,330 B1 | 6/2006 | Makower et al. | |
| 7,063,682 B1 | 6/2006 | Whayne et al. | |
| 7,066,942 B2 | 6/2006 | Treace | |
| RE39,196 E | 7/2006 | Ying et al. | |
| 7,077,842 B1 * | 7/2006 | Cosman | A61B 18/148 128/898 |
| 7,081,122 B1 | 7/2006 | Reiley et al. | |
| 7,081,161 B2 | 7/2006 | Genge et al. | |
| 7,091,258 B2 | 8/2006 | Neubert et al. | |
| 7,091,260 B2 | 8/2006 | Kühn | |
| 7,094,202 B2 | 8/2006 | Nobis et al. | |
| 7,094,286 B2 | 8/2006 | Liu | |
| 7,108,696 B2 | 9/2006 | Daniel et al. | |
| 7,109,254 B2 | 9/2006 | Müller et al. | |
| 7,112,205 B2 | 9/2006 | Carrison | |
| 7,114,501 B2 | 10/2006 | Johnson et al. | |
| 7,138,442 B2 | 11/2006 | Smith et al. | |
| 7,153,306 B2 | 12/2006 | Ralph et al. | |
| 7,153,307 B2 | 12/2006 | Scribner et al. | |
| 7,156,843 B2 | 1/2007 | Skarda | |
| 7,156,845 B2 | 1/2007 | Mulier | |
| 7,160,296 B2 | 1/2007 | Pearson et al. | |
| 7,166,121 B2 | 1/2007 | Reiley et al. | |
| 7,172,629 B2 | 2/2007 | McKay et al. | |
| 7,179,255 B2 | 2/2007 | Lettice et al. | |
| 7,186,234 B2 | 3/2007 | Dahla et al. | |
| 7,186,761 B2 | 3/2007 | Soffiati et al. | |
| 7,226,481 B2 | 6/2007 | Kuslich et al. | |
| 7,252,671 B2 | 8/2007 | Scribner et al. | |
| 7,267,683 B2 | 9/2007 | Sharkey et al. | |
| 7,270,661 B2 | 9/2007 | Dahla et al. | |
| 7,294,127 B2 | 11/2007 | Leung | |
| 7,465,318 B2 | 12/2008 | Sennett et al. | |
| 7,480,533 B2 | 1/2009 | Cosman et al. | |
| 7,503,920 B2 | 3/2009 | Siegal | |
| 7,544,196 B2 | 6/2009 | Bagga et al. | |
| 7,559,932 B2 | 7/2009 | Truckai et al. | |
| 7,569,054 B2 | 8/2009 | Michelson | |
| 7,572,263 B2 | 8/2009 | Preissman | |
| 7,591,822 B2 | 9/2009 | Olson, Jr. et al. | |
| 7,625,364 B2 | 12/2009 | Corcoran et al. | |
| 7,641,664 B2 | 1/2010 | Pagano | |
| 7,731,720 B2 | 6/2010 | Sand et al. | |
| 7,811,291 B2 | 10/2010 | Liu et al. | |
| 7,824,403 B2 | 11/2010 | Vaska | |
| 7,842,041 B2 | 11/2010 | Liu et al. | |
| 7,887,543 B2 | 2/2011 | Sand et al. | |
| 7,905,884 B2 | 3/2011 | Simonton et al. | |
| 7,918,874 B2 | 4/2011 | Siegal | |
| 7,972,340 B2 | 7/2011 | Sand et al. | |
| 7,976,542 B1 | 7/2011 | Cosman | |
| 8,034,071 B2 | 10/2011 | Scribner et al. | |
| 8,246,627 B2 | 8/2012 | Vanleeuwen et al. | |
| 8,518,036 B2 | 8/2013 | Leung et al. | |
| 8,583,260 B2 | 11/2013 | Knudson | |
| 8,591,507 B2 | 11/2013 | Kramer et al. | |
| 8,663,226 B2 | 3/2014 | Germain | |
| RE44,883 E | 5/2014 | Cha | |
| 8,758,349 B2 | 6/2014 | Germain et al. | |
| 8,827,981 B2 | 9/2014 | Liu et al. | |
| 8,864,760 B2 | 10/2014 | Kramer et al. | |
| 8,936,631 B2 | 1/2015 | Nguyen | |
| 9,113,974 B2 | 8/2015 | Germain | |
| 9,125,671 B2 | 9/2015 | Germain et al. | |
| 9,161,809 B2 | 10/2015 | Germain et al. | |
| 9,421,057 B2 | 8/2016 | Germain | |
| 9,743,938 B2 | 8/2017 | Germain et al. | |
| 2001/0011174 A1 | 8/2001 | Reiley et al. | |
| 2001/0023349 A1 | 9/2001 | Van Tassel et al. | |
| 2002/0007180 A1 | 1/2002 | Wittenberger et al. | |
| 2002/0013600 A1 | 1/2002 | Scribner et al. | |
| 2002/0016583 A1 | 2/2002 | Cragg | |
| 2002/0026195 A1 | 2/2002 | Layne et al. | |
| 2002/0026197 A1 | 2/2002 | Foley et al. | |
| 2002/0068929 A1 | 6/2002 | Zvuloni | |
| 2002/0068974 A1 | 6/2002 | Kuslich et al. | |
| 2002/0077595 A1 | 6/2002 | Hundertmark et al. | |
| 2002/0082605 A1 | 6/2002 | Reiley et al. | |
| 2002/0115742 A1 | 8/2002 | Trieu et al. | |
| 2002/0128638 A1 | 9/2002 | Chauvel et al. | |
| 2002/0133148 A1 | 9/2002 | Daniel et al. | |
| 2002/0156483 A1 | 10/2002 | Voellmicke et al. | |
| 2002/0188299 A1 | 12/2002 | Reiley et al. | |
| 2002/0188300 A1 | 12/2002 | Arramon et al. | |
| 2003/0014094 A1 | 1/2003 | Hammack et al. | |
| 2003/0032929 A1 | 2/2003 | McGuckin | |
| 2003/0036763 A1 | 2/2003 | Bhatnagar et al. | |
| 2003/0043963 A1 | 3/2003 | Yamagami et al. | |
| 2003/0050644 A1 | 3/2003 | Boucher et al. | |
| 2003/0069522 A1 | 4/2003 | Jasobsen et al. | |
| 2003/0073979 A1 | 4/2003 | Naimark et al. | |
| 2003/0130664 A1 | 7/2003 | Boucher et al. | |
| 2003/0163085 A1 | 8/2003 | Tanner et al. | |
| 2003/0171744 A1 | 9/2003 | Leung et al. | |
| 2003/0191489 A1 | 10/2003 | Reiley et al. | |
| 2003/0195547 A1 | 10/2003 | Scribner et al. | |
| 2003/0212394 A1 | 11/2003 | Pearson et al. | |
| 2003/0212395 A1 | 11/2003 | Woloszko et al. | |
| 2003/0220414 A1 | 11/2003 | Axen et al. | |
| 2003/0225432 A1 | 12/2003 | Baptiste et al. | |
| 2003/0233096 A1 | 12/2003 | Osorio et al. | |
| 2004/0023384 A1 | 2/2004 | Fukaya | |
| 2004/0023784 A1 | 2/2004 | Yu et al. | |
| 2004/0024081 A1 | 2/2004 | Trieu et al. | |
| 2004/0024398 A1 | 2/2004 | Hovda et al. | |
| 2004/0024409 A1 | 2/2004 | Sand et al. | |
| 2004/0024410 A1 | 2/2004 | Olson et al. | |
| 2004/0034384 A1 | 2/2004 | Fukaya | |
| 2004/0044096 A1 | 3/2004 | Smith et al. | |
| 2004/0044350 A1 | 3/2004 | Martin et al. | |
| 2004/0059328 A1 | 3/2004 | Daniel et al. | |
| 2004/0087936 A1 | 5/2004 | Stern et al. | |
| 2004/0087994 A1 | 5/2004 | Suddaby | |
| 2004/0092946 A1 | 5/2004 | Bagga et al. | |
| 2004/0097612 A1 | 5/2004 | Rosenberg et al. | |
| 2004/0111136 A1 | 6/2004 | Sharkey et al. | |
| 2004/0127987 A1 | 7/2004 | Evans et al. | |
| 2004/0133208 A1 | 7/2004 | Weikel et al. | |
| 2004/0138758 A1 | 7/2004 | Evans et al. | |
| 2004/0153064 A1 | 8/2004 | Foley et al. | |
| 2004/0153115 A1 | 8/2004 | Reiley et al. | |
| 2004/0158237 A1 | 8/2004 | Abboud et al. | |
| 2004/0167561 A1 | 8/2004 | Boucher et al. | |

(56) References Cited

U.S. PATENT DOCUMENTS

| | | |
|---|---|---|
| 2004/0167562 A1 | 8/2004 | Osorio et al. |
| 2004/0167625 A1 | 8/2004 | Beyar et al. |
| 2004/0210231 A1 | 10/2004 | Broucher et al. |
| 2004/0215343 A1 | 10/2004 | Hochschuler et al. |
| 2004/0220577 A1 | 11/2004 | Cragg |
| 2004/0220680 A1 | 11/2004 | Yamamoto et al. |
| 2004/0225296 A1 | 11/2004 | Reiss et al. |
| 2004/0226479 A1 | 11/2004 | Lyles et al. |
| 2004/0230309 A1 | 11/2004 | Dimauro et al. |
| 2004/0236186 A1 | 11/2004 | Chu |
| 2004/0247644 A1 | 12/2004 | Bratt et al. |
| 2004/0267271 A9 | 12/2004 | Scribner et al. |
| 2005/0027245 A1 | 2/2005 | Sachdeva et al. |
| 2005/0033303 A1 | 2/2005 | Chappuis et al. |
| 2005/0038383 A1 | 2/2005 | Kelley et al. |
| 2005/0038422 A1 | 2/2005 | Maurice |
| 2005/0043737 A1 | 2/2005 | Reiley et al. |
| 2005/0055030 A1 | 3/2005 | Falahee |
| 2005/0060030 A1 | 3/2005 | Lashinski et al. |
| 2005/0070844 A1 | 3/2005 | Chow et al. |
| 2005/0070912 A1 | 3/2005 | Voellmicke |
| 2005/0070915 A1 | 3/2005 | Mazzuca et al. |
| 2005/0090852 A1 | 4/2005 | Layne et al. |
| 2005/0113836 A1 | 5/2005 | Lozier et al. |
| 2005/0119650 A1 | 6/2005 | Sanders et al. |
| 2005/0124989 A1 | 6/2005 | Suddaby |
| 2005/0143827 A1 | 6/2005 | Globerman et al. |
| 2005/0177168 A1 | 8/2005 | Brunnett et al. |
| 2005/0177210 A1 | 8/2005 | Lueng et al. |
| 2005/0182412 A1 | 8/2005 | Johnson et al. |
| 2005/0182413 A1 | 8/2005 | Johnson et al. |
| 2005/0187556 A1 | 8/2005 | Stack et al. |
| 2005/0199156 A1 | 9/2005 | Khairoun et al. |
| 2005/0209557 A1 | 9/2005 | Carroll et al. |
| 2005/0216018 A1 | 9/2005 | Senneii |
| 2005/0228391 A1 | 10/2005 | Levy et al. |
| 2005/0234425 A1 | 10/2005 | Miller et al. |
| 2005/0240193 A1 | 10/2005 | Layne et al. |
| 2005/0251266 A1 | 11/2005 | Maspero et al. |
| 2005/0251267 A1 | 11/2005 | Winterbottom et al. |
| 2005/0261683 A1 | 11/2005 | Veldhuizen et al. |
| 2005/0283148 A1 | 12/2005 | Janssen |
| 2005/0287771 A1 | 12/2005 | Seamons et al. |
| 2006/0024348 A1 | 2/2006 | Engqvist et al. |
| 2006/0025763 A1 | 2/2006 | Nelson et al. |
| 2006/0041033 A1 | 2/2006 | Bisig et al. |
| 2006/0052743 A1 | 3/2006 | Reynolds |
| 2006/0064101 A1 | 3/2006 | Arramon |
| 2006/0074433 A1 | 4/2006 | McGill et al. |
| 2006/0084977 A1 | 4/2006 | Lieberman |
| 2006/0085009 A1 | 4/2006 | Truckai et al. |
| 2006/0100635 A1 | 5/2006 | Reiley et al. |
| 2006/0100706 A1 | 5/2006 | Shadduck et al. |
| 2006/0106392 A1 | 5/2006 | Embry |
| 2006/0106459 A1 | 5/2006 | Truckai et al. |
| 2006/0116689 A1 | 6/2006 | Albans et al. |
| 2006/0116690 A1 | 6/2006 | Pagano |
| 2006/0122623 A1 | 6/2006 | Truckai et al. |
| 2006/0142732 A1 | 6/2006 | Karmarkar et al. |
| 2006/0149268 A1 | 7/2006 | Truckai et al. |
| 2006/0149281 A1 | 7/2006 | Reiley et al. |
| 2006/0156959 A1 | 7/2006 | Engqvist et al. |
| 2006/0184106 A1 | 8/2006 | McDaniel et al. |
| 2006/0184192 A1 | 8/2006 | Markworth et al. |
| 2006/0200121 A1 | 9/2006 | Mowery |
| 2006/0206116 A1 | 9/2006 | Yeung |
| 2006/0206136 A1 | 9/2006 | Sachdeva et al. |
| 2006/0217704 A1 | 9/2006 | Cockburn et al. |
| 2006/0217736 A1 | 9/2006 | Kaneko |
| 2006/0229625 A1 | 10/2006 | Truckai et al. |
| 2006/0229631 A1 | 10/2006 | Reiley et al. |
| 2006/0235417 A1 | 10/2006 | Sala |
| 2006/0259023 A1 | 11/2006 | Abboud et al. |
| 2006/0264819 A1 | 11/2006 | Fischer et al. |
| 2006/0264945 A1 | 11/2006 | Edidin et al. |
| 2006/0266372 A1 | 11/2006 | Miller et al. |
| 2006/0270750 A1 | 11/2006 | Almen et al. |
| 2006/0271061 A1 | 11/2006 | Beyar et al. |
| 2006/0276797 A1 | 12/2006 | Botimer |
| 2006/0276819 A1 | 12/2006 | Osorio et al. |
| 2006/0293687 A1 | 12/2006 | Bogert |
| 2007/0006692 A1 | 1/2007 | Phan |
| 2007/0010845 A1 | 1/2007 | Gong et al. |
| 2007/0016130 A1 | 1/2007 | Leeflang et al. |
| 2007/0016211 A1 | 1/2007 | Botimer |
| 2007/0021769 A1 | 1/2007 | Scribner et al. |
| 2007/0043373 A1 | 2/2007 | Sala |
| 2007/0055201 A1 | 3/2007 | Seto et al. |
| 2007/0055260 A1 | 3/2007 | Cragg |
| 2007/0055266 A1 | 3/2007 | Osorio et al. |
| 2007/0055275 A1 | 3/2007 | Schaller |
| 2007/0055277 A1 | 3/2007 | Osorio et al. |
| 2007/0055278 A1 | 3/2007 | Osorio et al. |
| 2007/0055279 A1 | 3/2007 | Sand et al. |
| 2007/0055281 A1 | 3/2007 | Osorio et al. |
| 2007/0055283 A1 | 3/2007 | Scribner |
| 2007/0055284 A1 | 3/2007 | Osorio |
| 2007/0055285 A1 | 3/2007 | Osorio et al. |
| 2007/0055300 A1 | 3/2007 | Osorio et al. |
| 2007/0055382 A1 | 3/2007 | Osorio et al. |
| 2007/0059281 A1 | 3/2007 | Moseley et al. |
| 2007/0067034 A1 | 3/2007 | Chirico et al. |
| 2007/0093840 A1 | 4/2007 | Pacelli |
| 2007/0114248 A1 | 5/2007 | Kovac |
| 2007/0118142 A1 | 5/2007 | Krueger et al. |
| 2007/0118143 A1 | 5/2007 | Ralph et al. |
| 2007/0142842 A1 | 6/2007 | Krueger et al. |
| 2007/0156130 A1 | 7/2007 | Thistle |
| 2007/0162042 A1 | 7/2007 | Dunker |
| 2007/0173939 A1 | 7/2007 | Kim et al. |
| 2007/0185231 A1 | 8/2007 | Liu |
| 2007/0197935 A1 | 8/2007 | Reiley |
| 2007/0198023 A1 | 8/2007 | Sand et al. |
| 2007/0203500 A1 | 8/2007 | Gordon |
| 2007/0211563 A1 | 9/2007 | Devries |
| 2007/0233146 A1 | 10/2007 | Henniges et al. |
| 2007/0260223 A1 | 11/2007 | Scheibe et al. |
| 2007/0260257 A1 | 11/2007 | Phan |
| 2007/0270876 A1 | 11/2007 | Kuo et al. |
| 2007/0276319 A1 | 11/2007 | Betts |
| 2007/0282305 A1 | 12/2007 | Goldfarb et al. |
| 2008/0004615 A1 | 1/2008 | Woloszko et al. |
| 2008/0015664 A1 | 1/2008 | Podjajsky |
| 2008/0033422 A1 | 2/2008 | Turner et al. |
| 2008/0058725 A1 | 3/2008 | Scribner et al. |
| 2008/0058821 A1 | 3/2008 | Maurer et al. |
| 2008/0058827 A1 | 3/2008 | Osorio et al. |
| 2008/0058840 A1 | 3/2008 | Albrecht |
| 2008/0065020 A1 | 3/2008 | Ralph et al. |
| 2008/0065087 A1 | 3/2008 | Osorio et al. |
| 2008/0065190 A1 | 3/2008 | Osorio et al. |
| 2008/0086142 A1 | 4/2008 | Kohm et al. |
| 2008/0140079 A1 | 6/2008 | Osorio et al. |
| 2008/0183165 A1 | 7/2008 | Buysee et al. |
| 2008/0183265 A1 | 7/2008 | Bly |
| 2008/0195112 A1 | 8/2008 | Liu et al. |
| 2008/0208255 A1 | 8/2008 | Siegal |
| 2008/0221608 A1 | 9/2008 | Betts |
| 2008/0228192 A1 | 9/2008 | Beyer et al. |
| 2008/0249481 A1 | 10/2008 | Crainich |
| 2008/0249525 A1 | 10/2008 | Lee et al. |
| 2008/0255571 A1 | 10/2008 | Truckai et al. |
| 2008/0269766 A1 | 10/2008 | Justis |
| 2008/0269796 A1 | 10/2008 | Reiley et al. |
| 2008/0287741 A1 | 11/2008 | Ostrovsky et al. |
| 2008/0294167 A1 | 11/2008 | Schumacher et al. |
| 2009/0076517 A1 | 3/2009 | Reiley et al. |
| 2009/0105775 A1 | 4/2009 | Mitchell et al. |
| 2009/0131867 A1 | 5/2009 | Liu et al. |
| 2009/0131886 A1 | 5/2009 | Liu et al. |
| 2009/0131945 A1 | 5/2009 | Liu et al. |
| 2009/0131948 A1 | 5/2009 | Liu |
| 2009/0131950 A1 | 5/2009 | Liu et al. |
| 2009/0131986 A1 | 5/2009 | Lee |

(56) References Cited

U.S. PATENT DOCUMENTS

| | | |
|---|---|---|
| 2009/0182427 A1 | 7/2009 | Liu et al. |
| 2009/0198243 A1 | 8/2009 | Melsheimer |
| 2009/0264862 A1 | 10/2009 | Neidert et al. |
| 2009/0264892 A1 | 10/2009 | Beyar et al. |
| 2009/0292289 A9 | 11/2009 | Sand et al. |
| 2009/0293687 A1 | 12/2009 | Nino et al. |
| 2009/0299282 A1 | 12/2009 | Lau et al. |
| 2010/0057087 A1 | 3/2010 | Cha |
| 2010/0076476 A1 | 3/2010 | To et al. |
| 2010/0082033 A1 | 4/2010 | Germain |
| 2010/0114184 A1 | 5/2010 | Degtyar |
| 2010/0121332 A1 | 5/2010 | Crainich et al. |
| 2010/0152724 A1 | 6/2010 | Marion et al. |
| 2010/0160922 A1 | 6/2010 | Liu et al. |
| 2010/0211076 A1 | 8/2010 | Germain et al. |
| 2010/0274270 A1 | 10/2010 | Patel |
| 2010/0298832 A1 | 11/2010 | Lau et al. |
| 2011/0034884 A9 | 2/2011 | Pellegrino et al. |
| 2011/0098701 A1 | 4/2011 | McIntyre et al. |
| 2011/0160737 A1 | 6/2011 | Steffen et al. |
| 2011/0251615 A1 | 10/2011 | Truckai et al. |
| 2011/0295261 A1 | 12/2011 | Germain |
| 2011/0295262 A1 | 12/2011 | Germain et al. |
| 2011/0301590 A1 | 12/2011 | Podhajsky et al. |
| 2012/0065543 A1 | 3/2012 | Ireland |
| 2012/0130381 A1 | 5/2012 | Germain |
| 2012/0143298 A1 | 6/2012 | Just et al. |
| 2012/0158004 A1 | 6/2012 | Burger et al. |
| 2012/0191095 A1 | 7/2012 | Burger et al. |
| 2012/0232553 A1 | 9/2012 | Bloom et al. |
| 2012/0239049 A1 | 9/2012 | Truckai |
| 2012/0265186 A1 | 10/2012 | Burger et al. |
| 2012/0277582 A1 | 11/2012 | Mafi |
| 2012/0277730 A1 | 11/2012 | Salahieh |
| 2012/0330180 A1 | 12/2012 | Pellegrino et al. |
| 2012/0330301 A1 | 12/2012 | Pellegrino et al. |
| 2013/0006232 A1 | 1/2013 | Pellegrino |
| 2013/0006257 A1 | 1/2013 | Lee |
| 2013/0041377 A1 | 2/2013 | Kuntz |
| 2013/0072941 A1 | 3/2013 | Tan-Malecki et al. |
| 2013/0231654 A1 | 9/2013 | Germain |
| 2013/0237795 A1 | 9/2013 | Carr |
| 2013/0261615 A1 | 10/2013 | Kramer et al. |
| 2013/0261621 A1 | 10/2013 | Kramer et al. |
| 2013/0345709 A1 | 12/2013 | Burger et al. |
| 2014/0135779 A1 | 5/2014 | Germain |
| 2014/0163566 A1 | 6/2014 | Phan et al. |
| 2014/0236144 A1 | 8/2014 | Krueger et al. |
| 2014/0257046 A1 | 9/2014 | Steven |
| 2014/0316413 A1 | 10/2014 | Burger et al. |
| 2014/0350542 A1 | 11/2014 | Kramer et al. |
| 2014/0371740 A1 | 12/2014 | Germain et al. |
| 2015/0216594 A1 | 8/2015 | Prakash |
| 2015/0265333 A1 | 9/2015 | Shin et al. |
| 2015/0297246 A1 | 10/2015 | Patel et al. |
| 2015/0313614 A1 | 11/2015 | Germain |
| 2016/0066984 A1 | 3/2016 | Janssen et al. |
| 2016/0228131 A1 | 8/2016 | Brockman et al. |
| 2016/0310193 A1 | 10/2016 | Lv et al. |
| 2017/0095291 A1 | 4/2017 | Harrington |
| 2017/0105798 A1 | 4/2017 | Allison |
| 2018/0078170 A1 | 3/2018 | Panescu et al. |
| 2018/0147006 A1 | 5/2018 | Purdy |
| 2018/0147007 A1* | 5/2018 | Purdy ............... A61B 18/1492 |
| 2019/0357971 A1 | 11/2019 | Adi et al. |
| 2020/0022709 A1 | 1/2020 | Burger et al. |
| 2020/0078066 A1 | 3/2020 | Purdy et al. |
| 2020/0146743 A1 | 5/2020 | Defosset et al. |
| 2020/0390449 A1 | 12/2020 | Purdy et al. |
| 2021/0236200 A1 | 8/2021 | McGregor et al. |
| 2021/0401496 A1 | 12/2021 | Purdy et al. |

FOREIGN PATENT DOCUMENTS

| | | |
|---|---|---|
| CN | 2841051 | 11/2006 |
| CN | 102500036 | 6/2012 |
| DE | 20314010 | 1/2015 |
| EP | 1459691 | 9/2004 |
| JP | 2004242936 | 9/2004 |
| JP | 2008510530 | 4/2008 |
| JP | 2008528081 | 7/2008 |
| JP | 2008541878 | 11/2008 |
| JP | 2010063887 | 3/2010 |
| JP | 2011500156 | 1/2011 |
| KR | 101342906 | 12/2013 |
| WO | 1993004634 | 3/1993 |
| WO | 1996013297 | 5/1996 |
| WO | 1996020752 | 7/1996 |
| WO | 1997003611 | 2/1997 |
| WO | 2002003870 | 1/2002 |
| WO | 2003101308 | 12/2003 |
| WO | 2005039390 | 5/2005 |
| WO | 2005122938 | 12/2005 |
| WO | 2007036815 | 4/2007 |
| WO | 2007087400 | 8/2007 |
| WO | 2008076330 | 6/2008 |
| WO | 2008084479 | 7/2008 |
| WO | 2009155319 | 12/2009 |
| WO | 2010039894 | 4/2010 |
| WO | 2010081187 | 7/2010 |
| WO | 2010135602 | 11/2010 |
| WO | 2010135606 | 11/2010 |
| WO | 2011066465 | 6/2011 |
| WO | 2011114602 | 9/2011 |
| WO | 2011137357 | 11/2011 |
| WO | 2011137377 | 11/2011 |
| WO | 2012071464 | 5/2012 |
| WO | 2013147990 | 10/2013 |
| WO | 2014093673 | 6/2014 |
| WO | 2016183178 | 11/2016 |

OTHER PUBLICATIONS

Notice of Allowance dated Mar. 31, 2021 for U.S. Appl. No. 15/822,864.
Office Action dated May 7, 2021 for U.S. Appl. No. 16/417,502.
International Search Report and Written Opinion dated Apr. 8, 2020 for PCT/US2019/060273.
European Examination Report dated Dec. 19, 2017 for EP13767383.6.
European Search Report dated Jan. 7, 2019 for EP16793433.0.
European Search Report dated Jun. 8, 2017 for EP17154660.9.
European Search Report dated Nov. 15, 2017 for EP09818476.5.
European Search Report dated Nov. 16, 2016 for EP14772615.2.
International Search Report and Written Opinion dated Jan. 9, 2012 for PCT/US2011/034185.
International Search Report and Written Opinion dated Jan. 22, 2009 for PCT/US2008/83698.
International Search Report and Written Opinion dated Feb. 7, 2018 for PCT/US2017/058303.
International Search Report and Written Opinion dated Feb. 21, 2018 for PCT/US2017/063281.
International Search Report and Written Opinion dated Mar. 30, 2018 for PCT/US2017/065328.
International Search Report and Written Opinion dated Apr. 23, 2016 for PCT/US2018/012372.
International Search Report and Written Opinion dated Jul. 20, 2010 for PCT/US2010/035687.
International Search Report and Written Opinion dated Jul. 26, 2011 for PCT/US2011/034628.
International Search Report and Written Opinion dated Aug. 25, 2009 for PCT/US2009/035726.
International Search Report and Written Opinion dated Nov. 20, 2009 for PCT/US2009/059113.
Notice of Allowance dated Jan. 4, 2017 for U.S. Appl. No. 13/302,927.
Notice of Allowance dated Jan. 18, 2017 for U.S. Appl. No. 13/097,998.

(56) References Cited

OTHER PUBLICATIONS

Notice of Allowance dated Feb. 21, 2019 for U.S. Appl. No. 14/139,372.
Notice of Allowance dated Apr. 3, 2019 for U.S. Appl. No. 15/349,715.
Notice of Allowance dated Apr. 9, 2014 for U.S. Appl. No. 12/578,455.
Notice of Allowance dated Apr. 23, 2018 for U.S. Appl. No. 13/083,411.
Notice of Allowance dated May 3, 2017 for U.S. Appl. No. 14/815,620.
Notice of Allowance dated May 11, 2018 for U.S. Appl. No. 14/453,427.
Notice of Allowance dated May 26, 2015 for U.S. Appl. No. 13/098,116.
Notice of Allowance dated Aug. 8, 2019 for U.S. Appl. No. 15/836,125.
Notice of Allowance dated Aug. 9, 2019 for U.S. Appl. No. 15/836,241.
Notice of Allowance dated Aug. 24, 2018 for U.S. Appl. No. 15/388,598.
Notice of Allowance dated Sep. 20, 2019 for U.S. Appl. No. 15/793,509.
Notice of Allowance dated Oct. 28, 2016 for U.S. Appl. No. 13/853,397.
Notice of Allowance dated Nov. 8, 2013 for U.S. Appl. No. 12/578,455.
Notice of Allowance dated Nov. 9, 2017 for U.S. Appl. No. 14/815,812.
Notice of Allowance dated Nov. 18, 2016 for U.S. Appl. No. 13/097,998.
Notice of Allowance dated Nov. 25, 2013 for U.S. Appl. No. 12/571,174.
Notice of Allowance dated Nov. 25, 2016 for U.S. Appl. No. 13/853,397.
Notice of Allowance dated Dec. 13, 2018 for U.S. Appl. No. 15/917,454.
Notice of Allowance dated Dec. 28, 2017 for U.S. Appl. No. 15/211,359.
Notice of Allowance dated Aug. 31, 2016 for U.S. Appl. No. 14/887,007.
Office Action dated Jan. 18, 2017 for U.S. Appl. No. 14/815,620.
Office Action dated Jan. 26, 2011 for U.S. Appl. No. 11/941,764.
Office Action dated Jan. 26, 2017 for U.S. Appl. No. 14/815,812.
Office Action dated Feb. 3, 2016 for U.S. Appl. No. 13/853,397.
Office Action dated Feb. 10, 2015 for U.S. Appl. No. 13/083,411.
Office Action dated Feb. 23, 2010 for U.S. Appl. No. 11/941,733.
Office Action dated Feb. 23, 2010 for U.S. Appl. No. 11/941,764.
Office Action dated Mar. 1, 2017 for U.S. Appl. No. 15/211,359.
Office Action dated Mar. 21, 2011 for U.S. Appl. No. 11/941,764.
Office Action dated Mar. 21, 2011 for U.S. Appl. No. 12/029,428.
Office Action dated Apr. 19, 2018 for U.S. Appl. No. 15/388,598.
Office Action dated Apr. 24, 2017 for U.S. Appl. No. 14/453,427.
Office Action dated Apr. 26, 2010 for U.S. Appl. No. 12/029,428.
Notice of Allowance dated May 27, 2021 for U.S. Appl. No. 15/822,944.
Office Action dated Feb. 27, 2013 for U.S. Appl. No. 12/578,455.
Office Action dated Jul. 12, 2016 for U.S. Appl. No. 14/887,007.
Office Action dated Sep. 10, 2013 for U.S. Appl. No. 12/571,174.
Disc-O-Tech confidence Cement System at http://www.disc-o-tech.com/Articles/Article.asp?CategoryID=4&ArticleID=168 accessed, ,Dec. 3, 2007.
Dai, et al., Bone-Particle-Impregnated Bone Cement: an in vivo weight-bearing study, Journal Biomedical Materials Search, vol. 25 ,Jul. 30, 1990 ,141-156.

Hasenwinkel, et al.,"A Novel High-Viscosity, Two-Solution Acrylic Bone Cement: Effect of Chemical Composition on Properties", J. Biomed Mater. Res. vol. 47, No. 1 ,1999 ,36-45.
Klawitter, et al., Application of Porous Ceramics for the Attachment of Load Bearing Internal Orthopedic Applications, J. Biomed. Mater. Res. Symp., 2(1) ,1972 ,61-229.
Liu, et al., Bone-Particle-Impregnanted Bone Cement: An In Vitro Study, Journal of Biomedical Materials Research, vol. 21 ,1987,247-261.
Park, et al., Biomaterials: An Introduction—Second Edition, Plenum Press ,1992 ,177-178.
Park, et al., The Materials Properties of Bone-Particle Impregnated PMMA, Journal of Biomedical Engineering, vol. 108, 1986, 141-148.
Office Action dated Nov. 27, 2020 for U.S. Appl. No. 15/822,944.
International Search Report and Written Opinion dated Apr. 8, 2020 for PCT/US2019060279.
Notice of Allowance dated Feb. 19, 2020 for U.S. Appl. No. 15/675,315.
European Search Report dated May 29, 2020 for EP17874650.9.
European Search Report dated Jun. 16, 2020 for EP17863626.2.
European Search Report dated Jul. 1, 2020 for EP17878602.6.
Office Action dated Jun. 10, 2020 for U.S. Appl. No. 15/822,944.
Office Action dated Jun. 11, 2020 for U.S. Appl. No. 15/822,864.
Office Action dated May 1, 2009 for U.S. Appl. No. 12/261,987.
Office Action dated May 5, 2010 for U.S. Appl. No. 11/941,764.
Office Action dated May 6, 2019 for U.S. Appl. No. 15/675,315.
Office Action dated May 13, 2009 for U.S. Appl. No. 12/029,428.
Office Action dated May 17, 2010 for U.S. Appl. No. 12/261,987.
Office Action dated May 21, 2014 for U.S. Appl. No. 13/098,116.
Office Action dated May 24, 2012 for U.S. Appl. No. 12/578,455.
Office Action dated May 31, 2016 for U.S. Appl. No. 14/815,620.
Office Action dated Jun. 4, 2018 for U.S. Appl. No. 15/349,715.
Office Action dated Jun. 8, 2009 for U.S. Appl. No. 11/941,764.
Office Action dated Jun. 12, 2009 for U.S. Appl. No. 11/941,733.
Office Action dated Jun. 21, 2013 for U.S. Appl. No. 13/215,098.
Office Action dated Jun. 22, 2018 for U.S. Appl. No. 15/917,454.
Office Action dated Jun. 25, 2015 for U.S. Appl. No. 13/853,397.
Office Action dated Jun. 29, 2018 for U.S. Appl. No. 15/449,591.
Office Action dated Jul. 11, 2017 for U.S. Appl. No. 14/815,812.
Office Action dated Jul. 12, 2010 for U.S. Appl. No. 11/941,764.
Office Action dated Jul. 12, 2017 for U.S. Appl. No. 13/083,411.
Office Action dated Jul. 25, 2011 for U.S. Appl. No. 11/941,733.
Office Action dated Jul. 29, 2013 for U.S. Appl. No. 13/098,116.
Office Action dated Jul. 30, 2013 for U.S. Appl. No. 13/083,411.
Office Action dated Sep. 1, 2010 for U.S. Appl. No. 12/029,428.
Office Action dated Sep. 6, 2017 for U.S. Appl. No. 15/211,359.
Office Action dated Sep. 26, 2017 for U.S. Appl. No. 15/388,598.
Office Action dated Oct. 2, 2018 for U.S. Appl. No. 14/139,372.
Office Action dated Oct. 30, 2018 for U.S. Appl. No. 15/349,715.
Office Action dated Nov. 3, 2008 for U.S. Appl. No. 11/941,764.
Office Action dated Nov. 3, 2008 for U.S. Appl. No. 12/029,428.
Office Action dated Nov. 5, 2008 for U.S. Appl. No. 11/941,733.
Office Action dated Nov. 7, 2019 for U.S. Appl. No. 15/675,315.
Office Action dated Nov. 12, 2013 for U.S. Appl. No. 13/083,411.
Office Action dated Nov. 25, 2016 for U.S. Appl. No. 13/083,411.
Office Action dated Dec. 2, 2009 for U.S. Appl. No. 12/029,428.
Office Action dated Dec. 3, 2012 for U.S. Appl. No. 12/571,174.
Office Action dated Dec. 9, 2009 for U.S. Appl. No. 12/262,064.
Office Action dated Dec. 11, 2009 for U.S. Appl. No. 12/261,987.
Office Action dated Dec. 20, 2019 for U.S. Appl. No. 15/862,441.
Office Action dated Dec. 26, 2019 for U.S. Appl. No. 15/822,864.
Notice of Allowance dated Feb. 7, 2022 for U.S. Appl. No. 16/680,056.
Office Action dated Nov. 29, 2021 for U.S. Appl. No. 16/677,124.

* cited by examiner

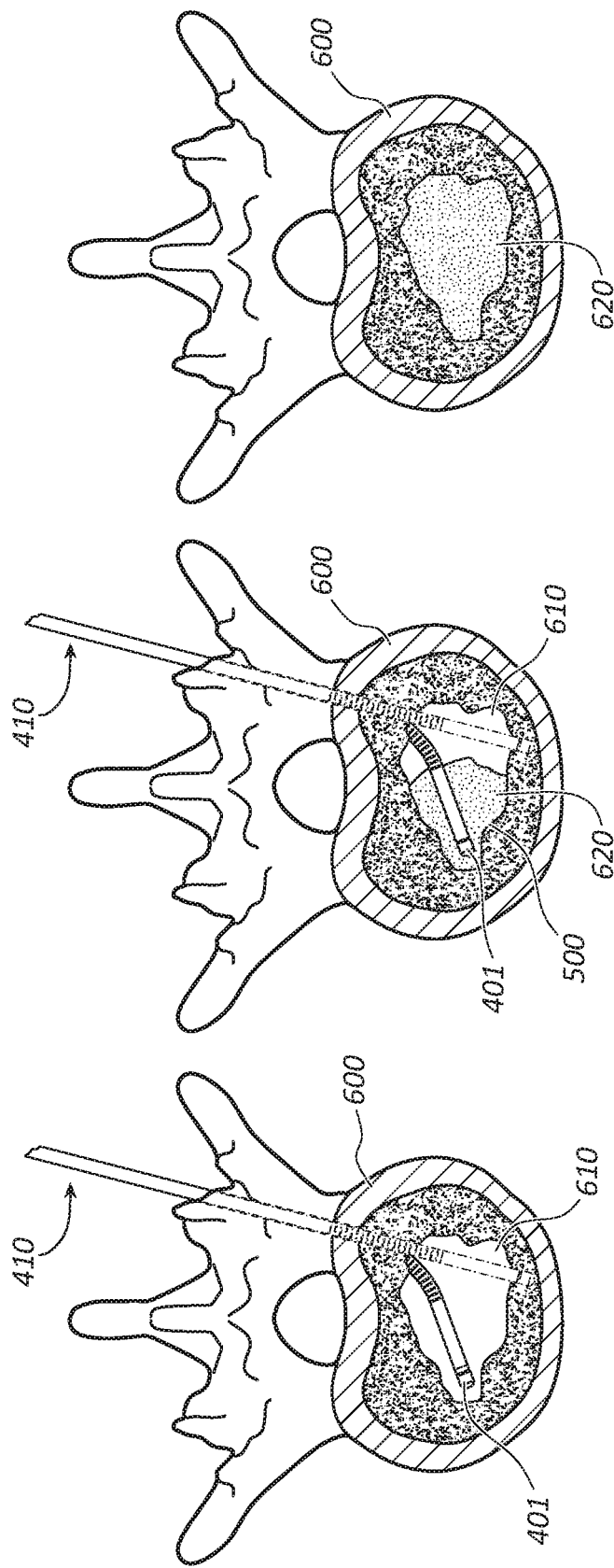

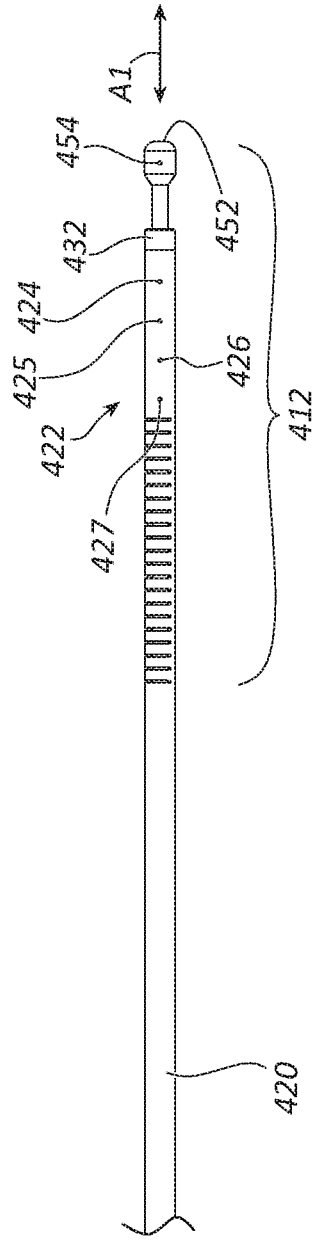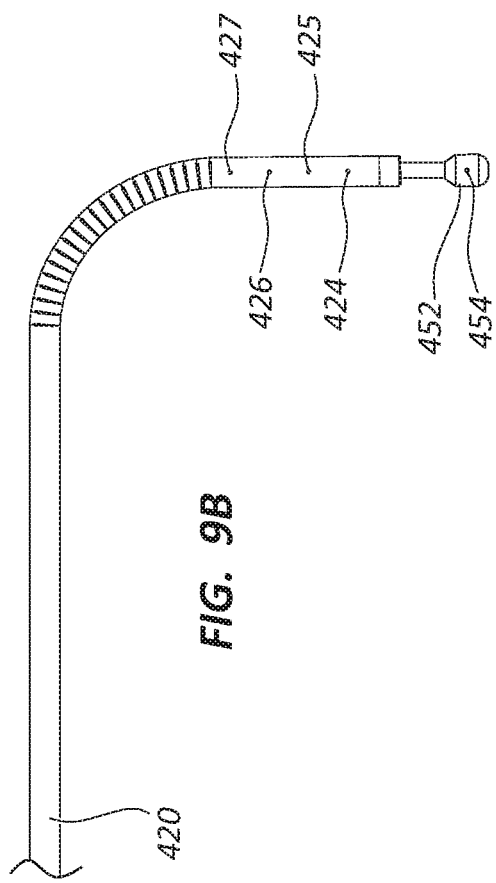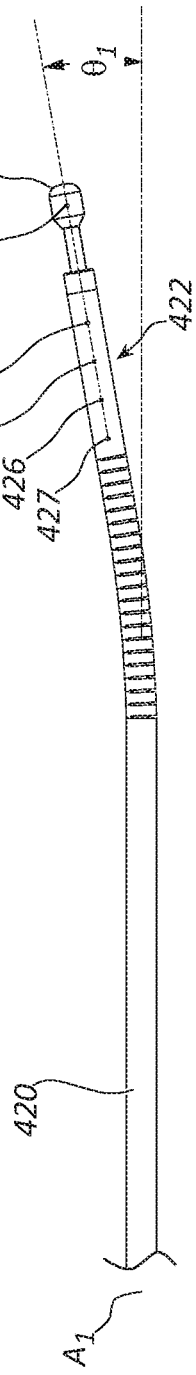

TUMOR ABLATION DEVICE AND RELATED SYSTEMS AND METHODS

RELATED APPLICATIONS

This application claims priority to U.S. Provisional Application No. 62/757,596, filed on Nov. 8, 2018 and titled "Tumor Ablation Device and Related Systems and Methods," and U.S. Provisional Application No. 62/757,578, filed on Nov. 8, 2018 and titled "Ablation Systems with Parameter-Based Modulation and Related Devices and Methods," both of which are incorporated herein by reference in their entireties.

TECHNICAL FIELD

The present disclosure relates generally to the field of medical devices. More particularly, some embodiments relate to spinal tumor ablation devices and related systems and methods. In some embodiments, the tumor ablation devices may be used to treat tumors or lesions in a patient's vertebra.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 4A is a schematic representation of the RF energy delivery probe of FIG. 1 being inserted into a vertebral body of a patient to treat a tumor or lesion using unipediclular vertebral access.

FIG. 4B is a schematic representation of the RF energy delivery probe of FIG. 1 delivering energy to ablate the tumor or lesion shown with a portion of the tumor or lesion ablated.

FIG. 4C is a schematic representation of dead tissue of the ablated tumor or lesion with the RF energy delivery probe removed from the vertebral body.

FIG. 9A is a side view of a portion of a RF (radiofrequency) energy delivery probe of the medical device of FIG. 1 in a straight configuration.

FIG. 9B is a side view of a portion of the RF (radiofrequency) energy delivery probe of FIG. 9A in an articulated configuration.

FIG. 9C is a side view of a portion of the RF (radiofrequency) energy delivery probe of FIG. 9A in a hyperextended configuration.

DETAILED DESCRIPTION

Figure 1:
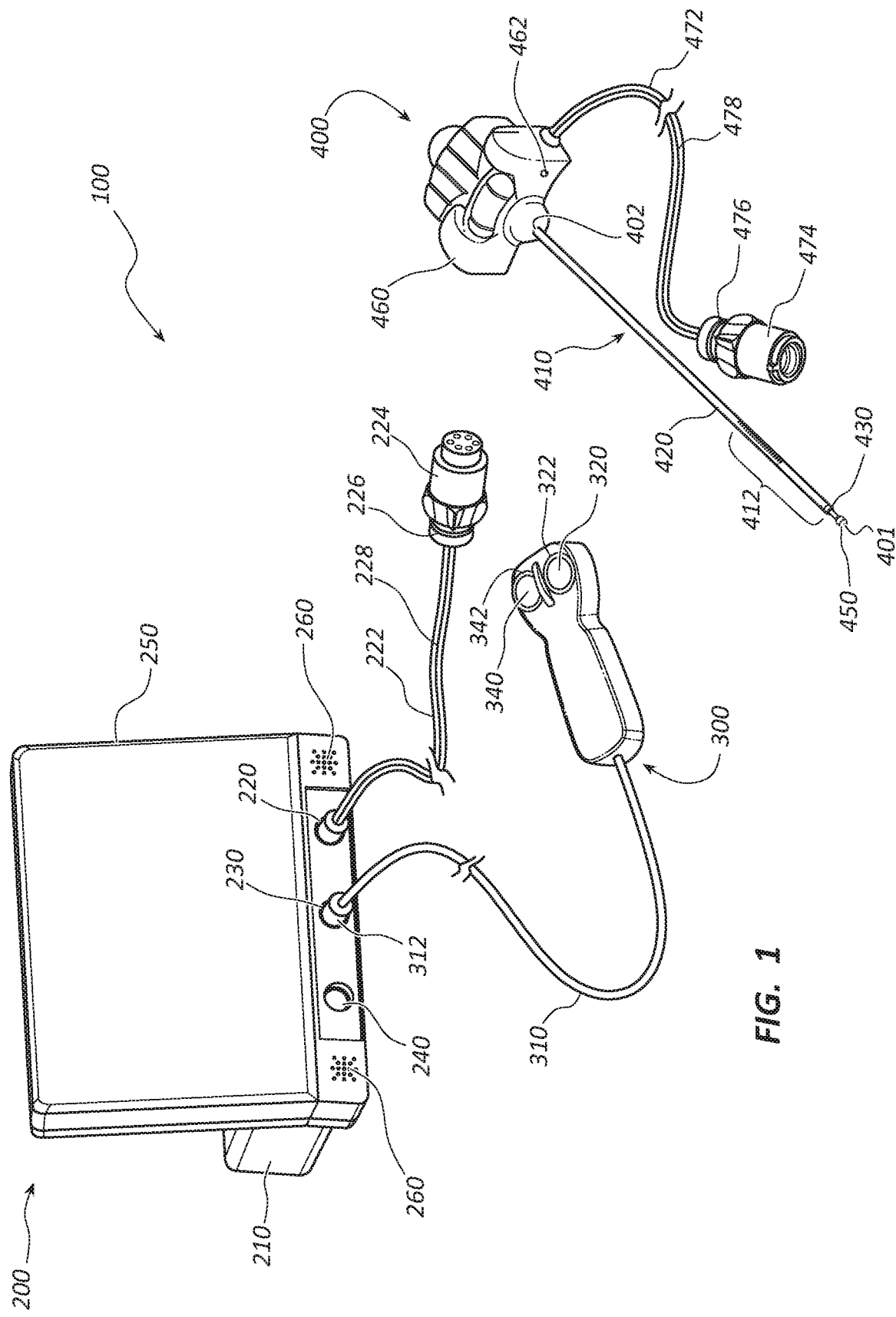
FIG. 1 is a perspective view of a tumor ablation system that includes a base unit, a remote, and a medical device.

Tumor ablation devices can be used to treat a tumor in a vertebra or other bones, such as the long bones of a patient. For example, in some embodiments, a distal end of a tumor ablation device may be inserted into a vertebra of a patient. Once the distal end of the tumor ablation device is inserted into the vertebra of the patient, an articulating distal portion of the tumor ablation device may be manipulated to position the tumor ablation device at a desired location within a tumor of the patient. The tumor ablation device may then be activated. Activation of the tumor ablation device may cause an electrical current (e.g., a radiofrequency current) to be applied to ablate tissue, such as the tumor. For instance, radiofrequency current may pass between a first electrode and a second electrode of the tumor ablation device. As the electrical current passes between the first electrode and the second electrode, the current may pass through tissue of the patient, thereby heating (and potentially killing) the adjacent tissue (e.g., tumor cells). The tumor ablation device may comprise one or more temperature sensors which may be used to measure the temperature of the heated tissue adjacent to the tumor ablation device. Based on the information obtained from the one or more temperature sensors, the duration, position, and/or magnitude of the delivered thermal energy may be tailored to ablate tumor tissue within a desired region of the tumor while avoiding the delivery of damaging amounts of thermal energy to healthy tissue. In some embodiments, once the tumor has been treated with thermal energy (e.g., converted radiofrequency energy), a cement may be delivered through with a different device to stabilize the vertebra of the patient.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities. Two components may be coupled to each other even though they are not in direct contact with each other. For example, two components may be coupled to one another through an intermediate component. The phrases "attached to" or "attached directly to" refer to interaction between two or more entities that are in direct contact with each other and/or are separated from each other only by a fastener of any suitable variety (e.g., an adhesive).

The terms "proximal" and "distal" are opposite directional terms. For example, the distal end of a device or component is the end of the component that is furthest from the practitioner during ordinary use. The proximal end refers to the opposite end, or the end nearest the practitioner during ordinary use.

FIG. 1 illustrates a tumor ablation system 100 for use in one or more medical procedures, such as procedures to treat a spinal tumor in one or more vertebral bodies of a patient. The tumor ablation system 100 however is not limited to treating spinal tumors in vertebral bodies, but may be used to treat tumors in various other locations in the body, such as the hip, pelvis, or other long bones. The tumor ablation system 100 may comprise a base unit 200, one or more medical devices 400 (or portions thereof) or medical device assemblies for use in a tumor ablation procedure, and a remote 300 that may enable a user to control energy delivery to the medical device 400, or other aspects of the medical device 400.

The base unit 200 may comprise a housing 210 that may house one or more power supplies (e.g., a radiofrequency ("RF") generator) that provides RF energy to a RF energy delivery probe 410 of the medical device 400. The base unit 200 may further comprise ports 220, 230, 240 that couple the medical devices 400 and the remote 300 to the base unit 200. The base unit 200 of FIG. 1 may include two power supplies (not shown) disposed in the housing 210. In the illustrated embodiment, one of the power supplies may correspond to port 220 and the other power supply may correspond to port 240. In other words, in some embodiments, each port 220, 240 may be electrically coupled to, and powered by, an independent power supply.

In some embodiments, the remote 300 may include a cable 310 and plug 312 that are configured to couple the remote 300 to the base unit 200 via port 230. This coupling may be configured to enable communication between the remote 300 and the base unit 200. In some embodiments, the port 230 may be a wireless port that wirelessly connects with the remote 300. The remote 300 may include a plurality of toggle buttons. The illustrated remote 300 of FIG. 1 illustrates two buttons 320 and 340. In the illustrated embodiment, toggle button 320 is configured to correspond with port 220 and a first power supply (RF generator) disposed in the housing 210 and button 340 is configured to correspond with port 240 and a second power supply (RF generator) disposed in the housing 210. Again, the two power supplies disposed in the housing 210 may be independent of each other. The toggle button 320 may thus be used toggle off and on the power supply (RF generator) corresponding to port 220 and thus toggle off and on energy delivery to a medical device coupled to port 220. Similarly, toggle button 340 may be configured to toggle off and on the delivery of energy to a medical device coupled to port 240.

The base unit 200 may further include a display 250 to display a user interface. The user interface may enable configuration of parameters, setting of preferences, and the like by a physician or other medical professional for the tumor ablation procedure. The user interface may further display a current state of the tumor ablation procedure.

Figure 5:
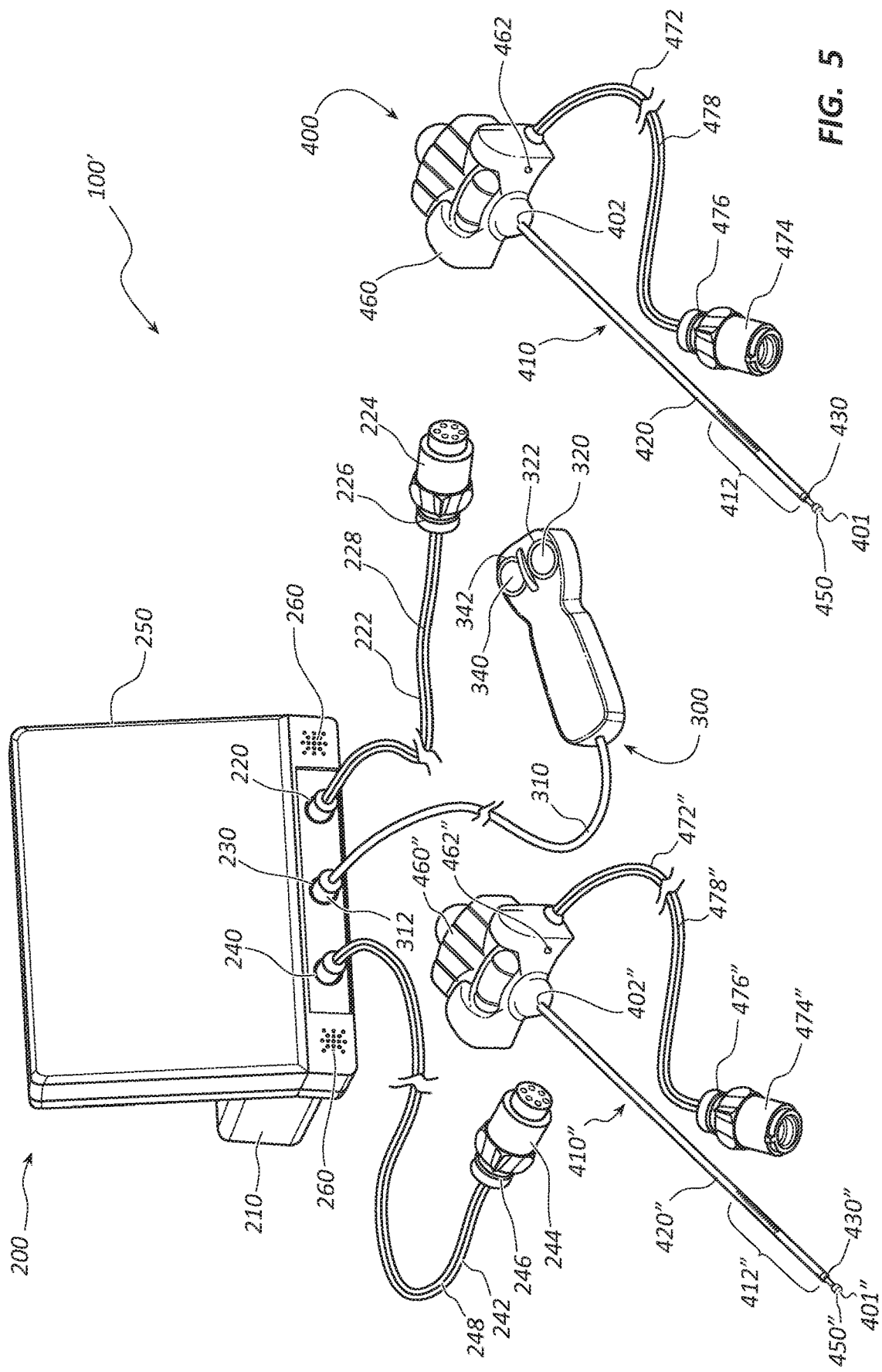
FIG. 5 is a perspective view of a tumor ablation system that includes a base unit, a remote, and a plurality of medical devices.

The tumor ablation system 100 may further include one or more medical devices 400 for performing a tissue ablation. FIG. 1 illustrates a single medical device 400 that may be used for single pedicle (unipedicular) vertebral access to treat a tumor or lesion. However, the tumor ablation system 100 may include more than one medical device 400. For example, FIG. 5 illustrates a tumor ablation system 100 with two medical devices 400 and 400' for performing a two pedicle (bipedicular) vertebral access to treat tumors or lesions.

In the illustrated embodiment, the medical device 400 includes, among other elements, an RF energy delivery probe 410 that includes a first or outer tubular conductor 420, a first or outer tubular insulator 430, a second or inner tubular insulator 440 (not shown in FIG. 1, see FIG. 2B), and a second or inner tubular conductor 450. The RF energy delivery probe 410 may extend from a proximal end 402 to a distal end 401.

The medical device 400 may further include a housing 460 and a cable 472 and plug 474 that is configured to couple the medical device 400 to the base unit 200 to enable communication between the medical device 400 and the base unit 200 and to provide electrical energy to the RF energy delivery probe 410. The base unit 200 may include an extension cable 222 and plug 224 that couples to port 220 or 240 and may extend the range of the RF energy delivery probe 410. In some embodiments, the cable and plug 474 may couple directly to port 220 or 240 without the use of the extension cable 222. As discussed above, each port 220 and 240 correspond with an independent power supply and medical device 400 may be coupled to either port 220 or 240 to access a power supply.

In the illustrated embodiment of FIG. 1, the tumor ablation system 100 is shown comprising a single medical device 400. The tumor ablation system 100 may include a plurality of identifying features that signify to a user which port (220 or 240) to which the medical device 400 is coupled. Systems within the scope of this disclosure may have any combination of the identifying features discussed below.

As detailed below, one or more portions of the medical device 400 or related components may have an indicator light or other feature that identifies the port (220 or 240) to which the medical device 400 is coupled. For example, the plug 474 may include a light 476 (e.g. LED) that lights up when the plug is coupled to either of the ports 220 and 240. For example, if the medical device 400 is coupled to port 220 the light 476 may light up a first color (e.g. blue). If the medical device 400 is coupled to port 240 the light 476 may light up a second color (e.g. white). The light 476 may be a ring that extends around the circumference of the plug 474.

Another identifying feature may be a light 478 (e.g. LED) disposed along the length of the cable 472. The light 478 of the cable 472 may light a first color (e.g. blue) when the medical device 400 is coupled to port 220 and may light up a second color (e.g. white) when the medical device 400 is coupled to port 240.

Similar identifying features may be disposed on the extension cable 222 and plug 224. For example, the plug 224 may include a light 226 (e.g. LED) that may light up a first color (e.g. blue) when the extension cable 222 and plug 224 are coupled to the port 220 and/or a medical device and may light up a second color (e.g. white) when the extension cable 222 and plug 224 are coupled to the port 240 and/or a medical device. The light 226 may be a ring that extends around the circumference of the plug 224. The cable 222 may include a light 228 that is disposed along the length of the extension cable 222 and the light 228 may light up a first color (e.g. blue) when cable 222 and plug 224 are coupled to the port 220 and/or a medical device and a second color (e.g. white) when the cable 222 and plug 224 are coupled to the port 240 and/or a medical device.

Another identifying feature may be a light 462 (e.g. LED) disposed on the housing 460 of the medical device 400. The light 462 of the housing 460 may light a first color (e.g. blue) when the medical device 400 is coupled to port 220 and may light up a second color (e.g. white) when the medical device 400 is coupled to port 240.

Another identifying feature may be disposed on the remote 300. The remote 300 may include lights that distinguish between which toggle button 320 and 340 correspond with each port 220 and 240. For example, toggle button 320 may include a light 322 (e.g. LED) that lights up a first color (e.g. blue) when the remote is coupled to or wirelessly connected to port 230. Toggle button 340 may include a light 342 (e.g. LED) that lights up a first color (e.g. white) when the remote 300 is coupled to or wirelessly connected to port 230. Unlike the other identifying features, the toggle buttons 320 and 340 do not alternate between colors but are color specific to the corresponding port. Accordingly, the user may always know which toggle button 320 and 340 corresponds to which port 220 and 240.

Again, the plurality of identifying features may be independent of the other identifying features or they may be in a number of different combinations. For example, in one embodiment, one of the lights 476, 478, 226, 228, and 462 may be used as the only identifying feature. In another embodiment, light 476 of the plug 474 may work in conjunction with the light 462 of the housing 460. A plurality of different combinations may be used in an attempt to help a physician identify which medical device is coupled to which port 220 and 240.

The base unit 200 may further include a plurality of speakers 260. The speakers 260 enable the base unit 200 to provide audible indicators to the user. For example, when a medical device is turned on and is coupled to port 220 and ablating, the base unit 200 may give a first audible indicator. If a second medical device is turned on and is coupled to port 240 and ablating, the base unit 200 may give a second audible indicator. The audible indicators are different from each other and the user would be able to know by sound if one or two medical devices are currently ablating.

Figure 2A:
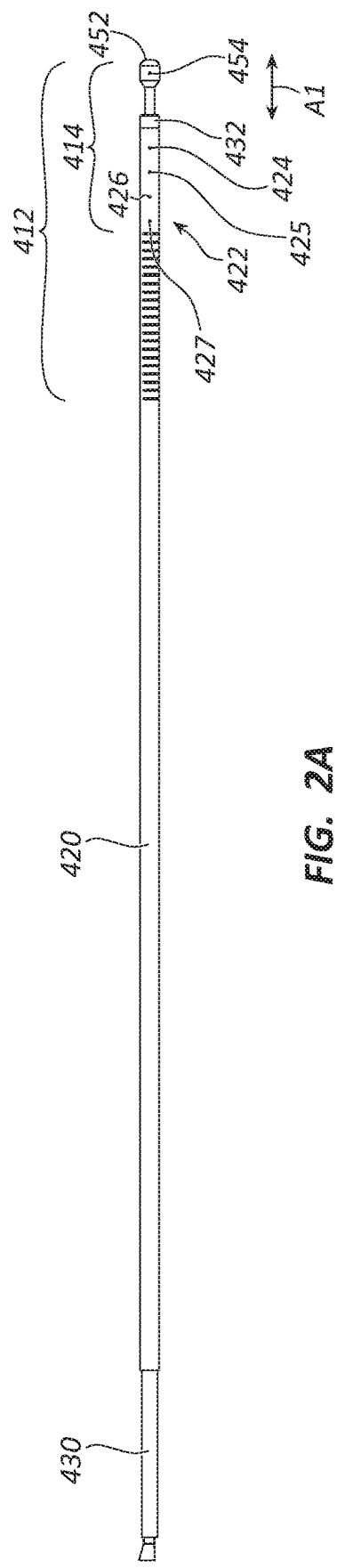
FIG. 2A is a side view of a RF (radiofrequency) energy delivery probe of the medical device of FIG. 1.
Figure 2B:
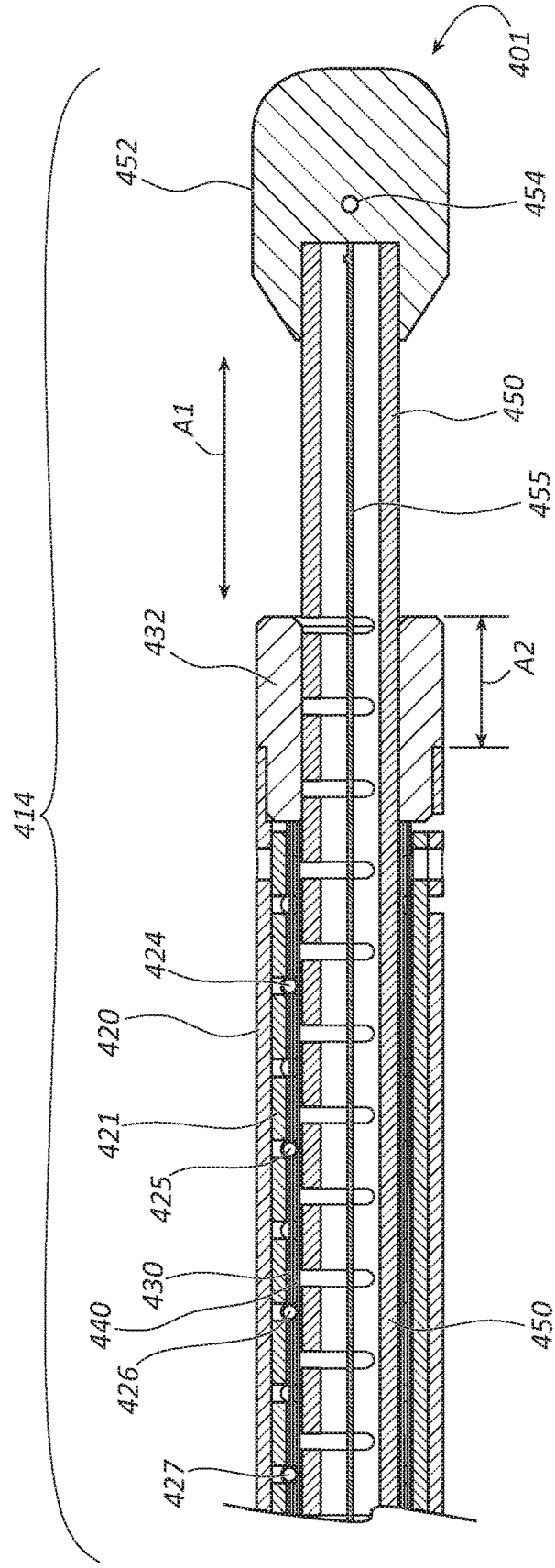
FIG. 2B is a cross-sectional view of the distal portion of the RF energy delivery probe of FIG. 2A.

FIGS. 2A-2B illustrate a probe of the medical device 400 in greater detail. FIG. 2A illustrates a side view of the RF energy delivery probe 410, and FIG. 2B illustrates a detailed cross-sectional view of the distal portion of the RF energy delivery probe 410. The RF energy delivery probe 410 may have a first pole or RF+ pole and a second pole, return pole, or RF− pole, the first tubular insulator 430, the second tubular insulator 440, and a primary insulator, or bushing insulator 432 that is disposed between the poles and may act as a bushing.

Though various elements of the embodiment of FIGS. 2A and 2B are referenced as "tubular" (e.g. the first tubular conductor 420, first tubular insulator 430, second tubular insulator 440, and second tubular conductor 450), other geometries of these elements are within the scope of this disclosure. That is, one or more of these elements may be configured with a non-tubular geometry in some embodiments. Further, tubular elements with various cross-sectional shapes, including round, square, rectangular, triangular, polygonal, and so forth are likewise within the scope of this disclosure. Additionally, tubular elements wherein the cross-sectional geometry or size varies along the length of the tubular element are within the scope of this disclosure.

The first tubular conductor 420 may be a metallic tube that extends from a proximal anchor (e.g., a metallic anchor) to an open distal end. The first tubular conductor 420 may act as the second pole (RF−). In some embodiments, a complimentary tubular conductor 421 may be disposed within the first tubular conductor 420. The complimentary tubular conductor may be metallic and may be physically and electrically connected to the first tubular conductor 420.

The first tubular insulator 430 may be at least partially disposed within the first tubular conductor 420. For example, the first tubular insulator 430 may extend through the first tubular conductor 420. More particularly, in some embodiments, the first tubular insulator 430 extends through the first tubular conductor 420 such that a proximal end of the first tubular insulator 430 is proximal of the first tubular conductor 420 and a distal end of the first tubular insulator 430 is proximal of the first tubular conductor 420. The first tubular insulator 430 and the second tubular insulator 440 may be made from any suitable insulating material, such as polymeric insulating materials. Examples of suitable polymeric insulating materials include polyimide, polycarbonate, polyetheretherketone (PEEK), and polyether block amides (e.g., PEBAX®). The first tubular insulator 430 may extend past the open of the first conductor 420 and may act as the primary insulator, or bushing insulator 432, e.g., bushing, between the first pole or RF+ pole and the second pole, return pole, or RF− pole. That is, the first tubular insulator 430 may extend a sufficient distance to function as an insulator along the portion of the exemplary embodiment where the bushing insulator 432 is disposed. In this way the first tubular insulator 430 may take the place of the bushing insulator 432, such that there is no separate element defining the bushing insulator 432. Additionally, in some embodiments, the first tubular insulator 430 may extend along the device and comprise an enlarged section that defines the bushing insulator 432. Thus, the first tubular insulator 430 and bushing insulator 432 may be a single part and may or may not have the same cross-sectional geometry and/or size. In other embodiments, the bushing insulator 432 may be a separate component from the first tubular insulator 430. In such a case, materials such as ceramics (Zirconia) may be considered.

The second tubular insulator 440 may be disposed within the first tubular insulator 430. For example, the second tubular insulator 440 may extend through the first tubular insulator 430. More particularly, in some embodiments, the second tubular insulator 440 extends through the first tubular insulator 430 such that a proximal end of the second tubular insulator 440 is proximal of the first tubular insulator 430 and a distal end of the second tubular insulator 440 is in line with the distal end of the first tubular insulator 430. The second tubular insulator 440 may be made from any suitable insulating material, such as polymeric insulating materials. Examples of suitable polymeric insulating materials include polyimide, polyetheretherketone (PEEK), and polyether block amides (e.g., PEBAX®). In some embodiments, the second tubular insulator 440 may act as the primary insulator or bushing insulator 432, e.g., bushing, between the first pole or RF+ pole and the second pole, return pole, or RF− pole. That is, as with the first tubular insulator 430, the second tubular insulator 440 may extend and form the bushing insulator 432 or may be a separate component from the bushing insulator 432.

The second tubular conductor 450 may be a metallic tube that extends from a proximal end (e.g., a metallic anchor) to a distal end. In some embodiments, the second tubular conductor 450 is rigid (or is rigid along most of its length). The second tubular conductor 450 may be at least partially disposed within the second tubular insulator 440. For example, the second tubular conductor 450 may extend through the second tubular insulator 440 such that a distal portion 452 of the second tubular conductor 450 is disposed distal of the first tubular conductor 420, the first tubular insulator 430, and the second tubular insulator 440. In some embodiments, the distal portion 452 of the second tubular conductor 450 that is disposed distal of the first tubular insulator 430 is longitudinally offset from the first tubular conductor 420 by the longitudinal length of the bushing insulator 432. The bushing insulator 432 may have a length A2 of between 0.1 cm and 0.5 cm. Stated differently, the gap between the distal portion 452 the second tubular conductor 450 and the distal end of the first tubular conductor 420 may be between 0.3 cm and 1.0 cm when the distal portion 452 is in a non-deployed or non-extended configuration, as further detailed below.

The distal portion 452 of the second tubular conductor 450 may act as the first probe electrode (RF+). The second tubular conductor 450 may extend and retract relative to the first tubular conductor 420. In some embodiments, the second tubular conductor 450 may extend and retract axially up to 8 mm, as shown by arrow A1. In some embodiments, the RF energy delivery probe 410 may extend and retract up to 5 mm. In some embodiments, the RF energy delivery probe 410 may extend and retract up to 1 mm. The axial movement of the RF energy delivery probe 410 may be controlled by the physician or by another medical professional and may be displayed on the display 250. The axial movement of the second tubular conductor 450 relative to the first tubular conductor 420 creates a continuous range of distances between the first tubular conductor 420 and the second tubular conductor 450. As discussed later, the extension and retraction of the second tubular conductor 450 relative to the first tubular conductor 420 affects the size of the ablation zones created by the RF energy delivery probe 410.

The RF energy delivery probe 410 may further comprise a plurality of thermocouples. In some embodiments, a distal thermocouple 454 may be disposed within the distal portion 452 of the second tubular conductor 450. The distal thermocouple 454 may be disposed near, or directly at, the maximum distal tip of the RF energy delivery probe 410 (meaning the distal-most point on the distal end 401 of the RF energy delivery probe 410). The distal thermocouple 454 may measure the temperature at the distal end 401 of the RF energy delivery probe 410. The temperature measured by the distal thermocouple 454 may be used for physician's reference and/or by a generator algorithm.

The RF energy delivery probe 410 may further comprise a plurality of thermocouples that are disposed proximal to the distal thermocouple 454. The illustrated embodiment of FIGS. 2A-2B illustrates four thermocouples that are proximal to the distal thermocouple 454. The thermocouples may be evenly spaced apart. A first proximal thermocouple 424 may be 5 mm back from the center of an ablation zone. A second proximal thermocouple 425 may be 10 mm back from the center of the ablation zone. A third proximal thermocouple 426 may be 15 mm back from the center of the ablation zone. A fourth proximal thermocouple 427 may be 20 mm back from the center of the ablation zone. In some embodiments, the fourth proximal thermocouple 427 may be 17.5 mm back from the center of the ablation zone. The thermocouples 424, 425, 426, 427 may be disposed between the first tubular insulator 430 and the second tubular insulator 440. Further, more or fewer thermocouples, positioned at different relative positions are also within the scope of this disclosure. For example, the thermocouples may be positioned at 5 mm intervals as described above or at 1 mm, 2 mm, 3 mm, 4 mm, or other intervals. Spacing wherein the offset between adjacent thermocouples is not constant along the plurality of thermocouples is also within the scope of this disclosure.

The temperatures measured by the proximal thermocouples 424, 425, 426, 427 and the temperature measured by the distal thermocouple 454 may be used for the physician's reference and/or may be employed by a generator algorithm. The algorithm may use the detected temperatures to create symmetric ablation zones that reach a predetermined temperature or thermal dose to ablate or kill the targeted tumor or lesions. Thermal dose is a function of temperature and exposure time.

In some embodiments, the first tubular conductor 420 is rigid (or is rigid along most of its length). In some embodiments, a distal portion of the first tubular conductor 420 includes a plurality of slots 422 proximal to the open distal end and the proximal thermocouples 424, 425, 426, and 427. The proximal thermocouples 424, 425, 426, and 427 and the distal thermocouple 454 are disposed on a rigid and straight section 414 of the RF energy delivery probe 410. The rigid and straight section 414 may be configured to enable the RF energy delivery probe 410 to create symmetric ablation regions. The slots 422 may be perpendicular or angled relative to the primary axis of the first tubular conductor 420. In other embodiments, the first tubular conductor 420 lacks a plurality of slots 422. Other geometries of the slots 422 not specifically described herein fall within the scope of the disclosure.

The slots 422 may enable the distal portion 412 of the RF energy delivery probe 410 to articulate. In some instances, articulation of the distal portion 412 of the RF energy delivery probe 410 may facilitate placement of the distal portion 412 of the RF energy delivery probe 410 at a desired location for ablation. Stated differently, the RF energy delivery probe 410 may have an active steering capability that enables navigation to and within a tumor. In some instances, articulation of the distal portion 412 of the RF energy delivery probe 410 may, additionally or alternatively, mechanically displace tissue (e.g., tumor cells) within the vertebra of the patient. For example, the RF energy delivery probe 410 may function as an articulating osteotome that enables site-specific cavity creation. Stated differently, the articulating distal portion 412 of the RF energy delivery probe 410 may be robust enough to facilitate navigation through hard tissue of a patient. The practitioner may be able to articulate a distal portion 412 of the RF energy delivery probe 410 such that the distal portion 412 transitions from a linear configuration to a non-linear configuration. Articulation of the distal portion 412 may be similar to articulation of the medical device described in U.S. patent application Ser. No. 15/822,864, filed Nov. 27, 2017, hereby incorporated by reference in its entirety.

In some embodiments, the articulation of the RF energy delivery probe 410 may be displayed on the display 250. Accordingly, the user may be able to see the extent of articulation during the procedure.

Figure 2C:
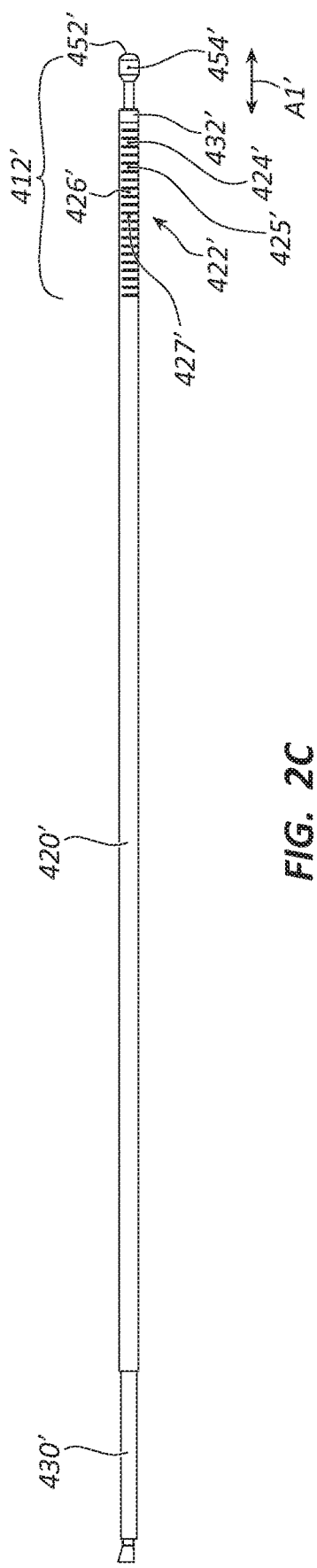
FIG. 2C is a side view of a RF (radiofrequency) energy delivery probe according to another embodiment.
Figure 2D:
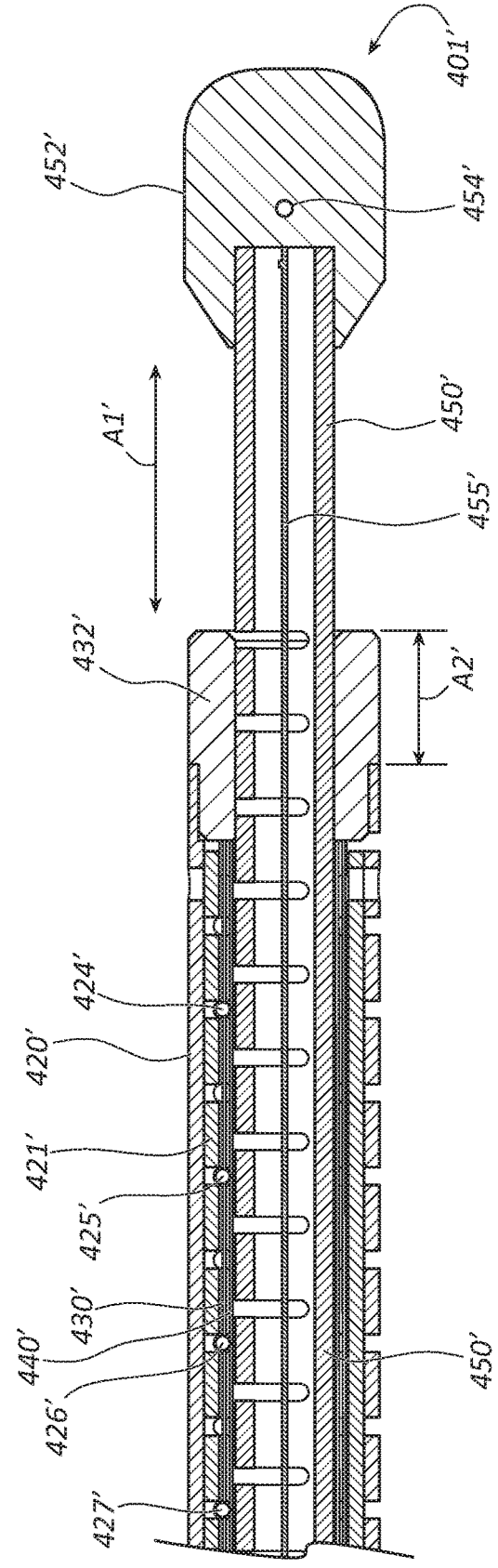
FIG. 2D is a cross-sectional view of the distal portion of the RF energy delivery probe of FIG. 2C.

FIGS. 2C-2D illustrate an alternative embodiment of the RF energy delivery probe 410' that include an articulating portion with a plurality of slots 422' that are adjacent to the open distal end and that corresponds with the proximal thermocouples 424', 425', 426', and 427'. The location of the articulating portion enables the RF energy delivery probe 410' to create a variety of different of ablation regions for ablating tumors.

FIGS. 3A-3D schematically illustrate a series of symmetric ablation zones 500a created by a RF energy delivery probe 410a. The symmetric ablation zones are symmetric about the poles of the first conductor 420 and the second conductor 450. The symmetric ablation zones 500a are three-dimensional, even though the FIGS. 3A-3D illustrate them as two-dimensional. As compared with the RF energy delivery probe 410 of FIGS. 1-2B, FIGS. 3A-3D illustrate variation on the design of the geometry of the distal tip of the RF energy delivery probe 410, thus the reference numerals in these figures are designated with a final letter "a" to indicate the variation with the prior embodiment. Nonetheless, disclosure related in connection with the embodiment of FIGS. 1-2B may be applied to the embodiment of FIGS. 3A-3D and vice versa. In the embodiment of FIGS. 3A-3D, a distal thermocouple 454a and proximal thermocouples 424a, 425a, 426a, 427a are shown in each of FIGS. 3A-3D.

Figure 3A:
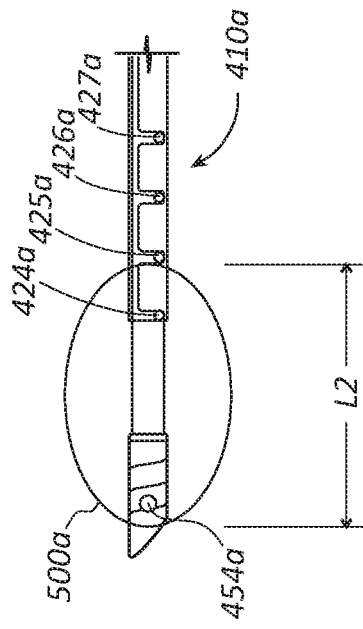
FIG. 3A is a schematic representation of a first exemplary ablation zone created by a RF energy delivery probe.
Figure 3B:
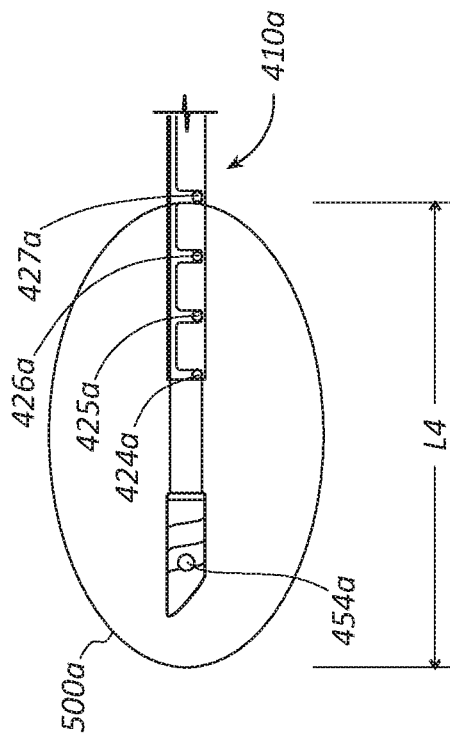
FIG. 3B is a schematic representation of a second exemplary ablation zone created by the RF energy delivery probe of FIG. 3A.
Figure 3C:
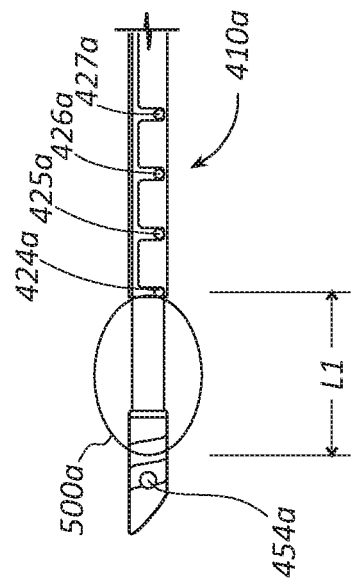
FIG. 3C is a schematic representation of a third exemplary ablation zone created by the RF energy delivery probe of FIG. 3A.
Figure 3D:
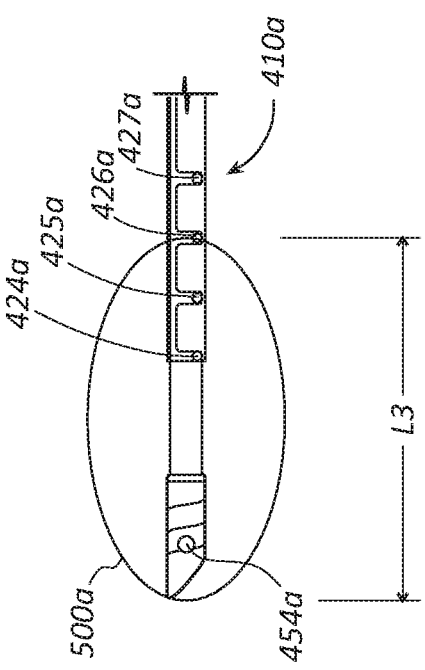
FIG. 3D is a schematic representation of a fourth exemplary ablation zone created by the RF energy delivery probe of FIG. 3A.

FIG. 3A illustrates a first ablation zone 500a with a length L1. In some embodiments, the length of L1 is 1 cm. FIG. 3B illustrates a second configuration where the ablation zone 500a has a length L2. In some embodiments, the length of L2 is 2 cm. FIG. 3C illustrates a third configuration where the ablation zone 500a has a length L3. In some embodiments, the length of L3 is 3 cm. FIG. 3D illustrates a fourth configuration where the ablation zone 500a has a length L4. In some embodiments, the length of L4 is 4 cm. In other embodiments, the length of L4 is 3.5 cm. While the present disclosure contemplates multiple ablation zone sizes, the present disclosure is not limited to these proposed ablation zone sizes. In fact, multiple ablation zone sizes are within the scope of these disclosure based on a single probe design.

The size of the ablation zone 500a may be controlled by modulating the delivery of electrical energy, such as radiofrequency energy, to the RF energy delivery probe 410a. In the illustrated embodiment, correlation between a 5 mm offset proximal thermocouples, 424a, 425a, 426a, and 427a, and 1 cm increments of the ablation zone size (due to 5 mm growth of the ablation zone 500a on each side of the distal tip of the RF energy delivery probe 410a) is shown. Again, in other embodiments, different sizes of ablation zone, including different increments for controlling the ablation zone 500a size, and different placement of the proximal thermocouples 424a, 425a, 426a, and 427a may be used.

The medical device may be configured to create symmetric ablation zones even when the RF energy delivery probe 410a is articulated along a distal portion (such as distal portion 412 of FIG. 1) because of the rigid and straight portion 414 where the thermocouples 424, 425, 426, and 427 are disposed.

FIGS. 4A-4C illustrate a method for treating a spinal tumor or lesion 610 in one or more vertebral bodies 600 of a patient using the medical device 400 of FIG. 1 by unipedicular access. For example, some embodiments of a medical procedure may comprise obtaining the medical device (400 of FIG. 1) and inserting the distal end 401 of the RF energy delivery probe 410 into a vertebral body of a patient (e.g., a sedated patient in the prone position). In some embodiments, the distal end 401 of the RF energy delivery probe 410 may be pointed and the pointed distal end 401 may facilitate penetration of bone within the vertebra of the patient. Further, in some embodiments, the RF energy delivery probe 410 has sufficient strength to prevent buckling of the RF energy delivery probe 410 as the distal end of the RF energy delivery probe 410 is inserted within a vertebra (e.g., across the cortical bone) of the patient. In some embodiments, the distal end 401 of the RF energy delivery probe 410 is inserted into the patient via an introducer (not shown).

In other embodiments, the distal end 401 of the RF energy delivery probe 410 may be inserted into the soft tissue of the patient without using an introducer.

FIG. 4A illustrates the RF energy delivery probe 410 inserted into the vertebra 600 of a patient with the tumor 610. The distal portion (412 of FIG. 1) of the RF energy delivery probe 410 may be articulated to place the RF energy delivery probe 410 in a predetermined position. The RF energy delivery probe 410 may be activated and the RF generator may provide energy for the RF energy delivery probe 410 to ablate the tumor 610. The RF energy delivery probe 410 may then create a symmetric ablation zone 500 (similar to the ablation zones 500a discussed in connection with FIGS. 3A-3D). With reference to FIG. 1 and FIGS. 2A-2B, the distal thermocouple 454 and the proximal thermocouples 424, 425, 426, 427 may detect the temperature of the surrounding tissue and provide the temperature feedback to the base unit 200, which may be displayed on the display 250. This information may then be fed into the generator algorithm to maintain a symmetric ablation zone to ablate the tumor 610 and avoid damaging surrounding tissue.

FIG. 4B illustrates ablated tissue 620 of the tumor 610 as the tissue reaches a predetermined temperature such as 50 degrees Celsius, or thermal dose. Once the tumor 610 reaches the predetermined temperature, the RF generator may turn off the power, or otherwise modify current delivery to the RF energy delivery probe 410. The diameter of the ablation zone 500 may be determined based on the size of the tumor 610. If the tumor 610 is smaller, the ablation zone 500 may be smaller and a subset of the proximal thermocouples 424, 425, 426, 427 may be used to detect the temperature in and immediately adjacent the ablation zone 500. If the ablation zone 500 is larger, all of the proximal thermocouples 424, 425, 426, 427 may be used to detect the temperature within and adjacent the ablation zone 500. That is to say, while all the proximal thermocouples 424, 425, 426, and 427 may monitor temperature and provide feedback to the base unit 200, in some procedures, only a subset of the proximal thermocouples 424, 425, 426, and 427 may be within and/or immediately adjacent the ablation zone 500. FIG. 4C illustrates the dead tissue 620 of the ablated tumor 610 with the RF energy delivery probe 410 removed from the vertebra 600 of the patient.

As discussed previously, FIG. 5 illustrates a tumor ablation system 100' with two medical devices 400 and 400" for performing a bipedicular vertebral access to treat tumors. In the illustrated embodiment, the tumor ablation system 100' comprises the base unit 200, remote 300, and medical device 400 of the tumor ablation system 100 of FIG. 1. That is to say, a tumor ablation system may be configured with a single medical device 400 or two medical devices 400 and 400", depending on the desired treatment. For clarity with connecting the disclosure of the tumor ablation system 100 and the tumor ablation system 100', the tumor ablation system 100' is shown as comprising the noted elements of the tumor ablation system 100. Embodiments wherein elements such as the base unit 200 and remote 300 are configured for use with only one, with one or two, with only two, or with other numbers of medical devices 400, 400" are likewise within the scope of this disclosure.

The second medical device, medical device 400", may be similar to the first medical device, medical device 400, or may be different based on treatment needs of the patient. The remote 300 may allow the user to adjust the energy provided to each medical device 400 and 400". In some embodiments, energy adjustment may be done automatically via an algorithm. For example, the remote 300 may have a button 320 for controlling the amount of energy to the medical device 400, 400" plugged into port 220 and a button 340 for controlling the amount of energy to the medical device 400, 400" plugged into port 240.

As discussed above, each medical device 400 and 400" may include a plurality of identifying features to help identify which medical device 400 and 400" is coupled to which port 220 and 240.

Figures 6A, 6B, 6C:
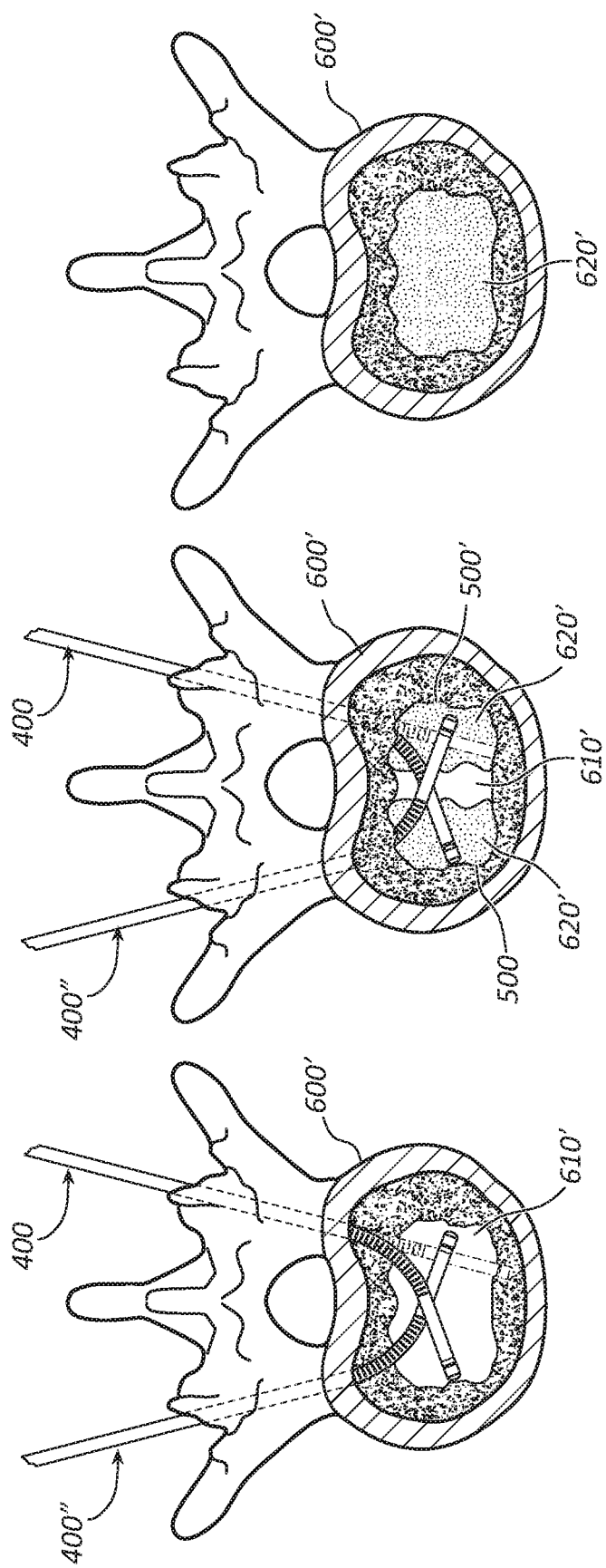
FIG. 6A is a schematic representation of two RF energy delivery probes being inserted into a vertebral body of a patient to treat a tumor or lesion using bipedicle vertebral access.
FIG. 6B is a schematic representation of two RF energy delivery probes delivering energy to ablate the tumor or lesion with a portion of the tumor or lesion ablated.
FIG. 6C is a schematic representation of dead tissue of the ablated tumor or lesion with two RF energy delivery probes removed from the vertebral body.

FIGS. 6A-6C illustrate a method for treating a spinal tumor 610' in one or more vertebral bodies 600' of a patient using the medical devices 400 and 400" using bipedicular access. For example, some embodiments of a medical procedure may involve obtaining the medical devices 400 and 400" and inserting the distal ends 401 and 401" of the RF energy delivery probes 410, 410" into a vertebral body of a patient (e.g., a sedated patient in the prone position). In other embodiments, the distal end 412 and 412" of the first tubular conductor 420 may be inserted into a vertebral body of the patient. In some embodiments, the distal ends 401 and 401" of the RF energy delivery probes 410, 410" or the distal end 412 and 412" of the first tubular conductor 420 may be pointed and the pointed distal ends may facilitate penetration of bone within the vertebra 600' of the patient. In some embodiments, the RF energy delivery probes 410, 410" have sufficient strength to prevent buckling of the RF energy delivery probes 410, 410" as the distal ends 401 and 401" of the RF energy delivery probes 410, 410" are inserted within the vertebra 600' (e.g., across the cortical bone) of the patient. In some embodiments, the distal ends 401 and 401" of the RF energy delivery probes 410, 410" are inserted into the patient via an introducer (not shown). In other embodiments, the distal ends 401 and 401" of the RF energy delivery probes 410, 410" may be inserted into the soft tissue of the patient without using an introducer.

FIG. 6A illustrates the medical devices 400 and 400" inserted into a vertebra 600' of a patient with a tumor 610'. The distal portions 412 and 412" of the RF energy delivery probes 410 and 410" may be articulated to place the RF energy delivery probes 410 and 410" in predetermined positions. The RF energy delivery probes 410 and 410" may be activated and the RF generator may provide energy to the RF energy delivery probes 410 and 410" to ablate the tumor 610'. The RF energy delivery probes 410 and 410" may each create symmetric ablation zones 500, 500', similar to the ablation zones 500 discussed in FIGS. 3A-3D. The distal thermocouples 454 and 454" and the proximal thermocouples 424, 425, 426, 427, 424", 425", 426", and 427" may detect the temperature of the surrounding tissue and provide the temperature feedback to the base unit 200, which may be displayed on the display 250. This information may be fed into the generator algorithm to maintain a symmetric ablation zone 500, 500' to ablate the tumor 610' and avoid damaging surrounding tissue.

FIG. 6B illustrates the ablated tissue 620' of the tumor 610' as the tissue reaches a predetermined thermal dose or temperature, such as 60 degrees Celsius. Once the tumor 610' reaches the predetermined temperature or thermal dose, the RF generator may turn off the power, or otherwise modify current delivery to the RF energy delivery probes 410 and 410". The diameter of the ablation zones 500, 500' may be determined based on the size of the tumor 610'. If the tumor 610' is smaller, the ablation zones 500, 500' may be smaller and only a subset of the proximal thermocouples 424, 425, 426, 427, 424", 425", 426", and 427" may be used to detect the temperature in and immediately adjacent the ablation zones 500, 500', as also described above in connection with FIG. 4B. FIG. 6C illustrates the dead tissue 620' of the ablated tumor 610' with the RF energy delivery probes 410 and 410' removed from the vertebra 600' of the patient.

Figure 7:
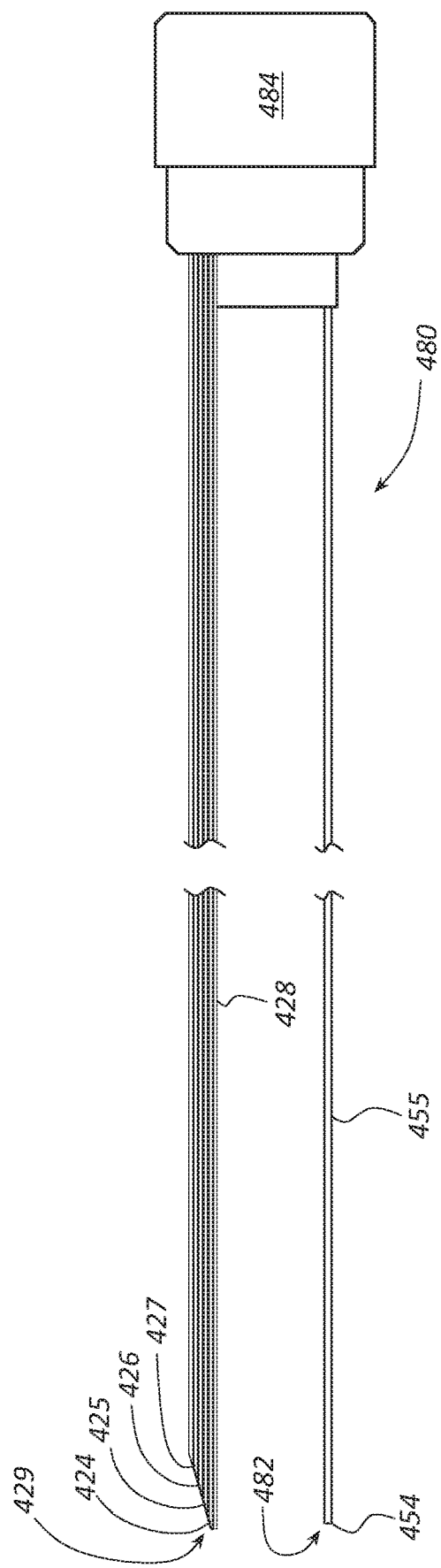
FIG. 7 is a schematic representation of a flexible or wired thermocouple circuit for the plurality of thermocouples.

FIG. 7 schematically illustrates a flexible thermocouple circuit 480 for the thermocouples 454, 424, 425, 426, and 427. (This disclosure may also be applied analogously to the thermocouples 454", 424", 425", 426", and 427" of the medical device 400".) The flexible thermocouple circuit 480 may be configured to provide flexibility and repeatability, enabling the flexible thermocouple circuit 480 to bend and articulate with the RF energy delivery probe 410. The flexible thermocouple circuit 480 may include a plurality of tails. In the illustrated embodiment, the flexible thermocouple circuit 480 has a first tail 428 and a second tail 455. The first tail 428 houses the thermocouples 424, 425, 426, and 427 at its distal end, with the thermocouples 424, 425, 426, and 427 spaced apart at a distal portion 429. As discussed previously, the thermocouples 424, 425, 426, and 427 may be evenly spaced apart or may be unevenly spaced apart. The first tail 428 may be disposed between the first tubular insulator 430 and the second tubular insulator 440.

The second tail 455 houses the distal thermocouple 454 at a distal portion 482. The second tail 455 is also illustrated in FIG. 2B, and the second tail 455 may extend along the inner diameter of the second tubular conductor 450 to the distal portion 452 of the second tubular conductor 450. In some embodiments, the first tail 428 may be thicker than the second tail 455.

Figure 8:
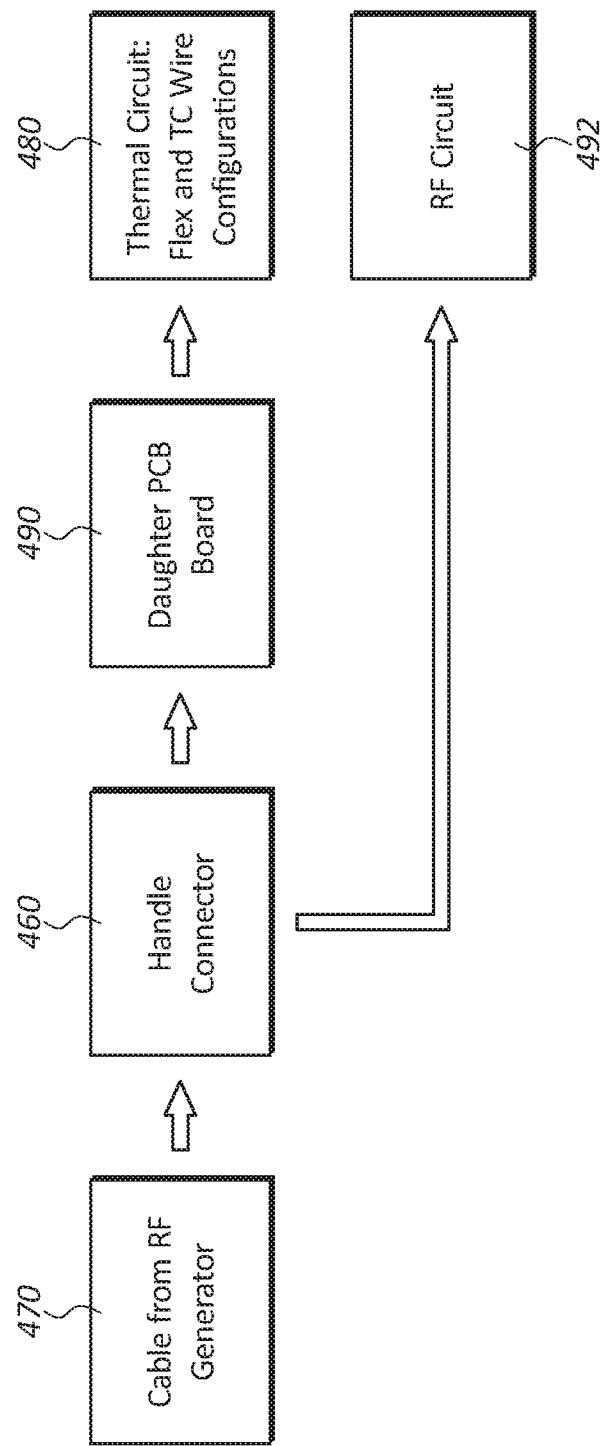
FIG. 8 is diagram of a circuit of the medical device.

FIG. 8 illustrates a flowchart for the different circuits of the tumor ablation system 100. The flexible thermocouple circuit 480 is configured to couple to a daughter board 490 that is disposed within the housing 460 of the medical device 400. The daughter board 490 is disposed within the housing 460 and is able to communicate with the base unit 200 via the cable and plug 470. Accordingly, the temperatures measured by the thermocouples 424, 425, 426, 427, 454 may be communicated to the base unit 200 and the RF generator algorithm. The flexible thermocouple circuit 480 may include a ZIF connector 484 for connecting the flexible thermocouple circuit 480 to a daughter board 490.

The daughter board 490 may further include a local cold junction compensation system. The temperature at the local cold junction is known, thereby making it possible to determine the temperatures at the thermocouples 424, 425, 426, 427, and 454. The local cold junction compensation system may comprise a thermistor or an integrated circuit.

The medical device 400 may further include an RF circuit 492 for delivery of the RF energy from the RF generator to the RF energy delivery probe 410.

The RF energy delivery probes discussed in the instant disclosure, such as RF energy delivery probe 410, may be used in various ablation procedures for treating tumors within a patient. The RF energy deliver probe 410 may be inserted within a patient to a tumor location. The tumor may be located in a variety of different areas within the patient. The RF energy delivery probe 410 may be guided to the tumor location via imaging, such as fluoroscopy, to ensure that the RF energy delivery probe 410 is delivered to the proper location. In some embodiments, the display 250 of the base unit 200 may display an overlay of the imaging and the position of the RF energy delivery probe 410.

The first conductor and the second conductor may be disposed within the tumor. RF energy may be delivered from the generator and produce a current between the first conductor and the second conductor. The first pole may be RF+ pole and the second pole may be a return pole, or RF− pole. As the electrical current passes between the first pole and the second pole, the current may pass through tissue of the patient (e.g., the ablation zone), thereby ablating by heating (and potentially killing) the adjacent tissue (e.g., tumor cells). The ablation zone created by the RF energy delivery probe 410 may be symmetric.

As discussed previously, the RF energy delivery probe 410 may comprise one or more thermocouples, 454, 424, 425, 426, and 427. Based on the temperature information obtained from the one or more thermocouples, 454, 424, 425, 426, and 427, the duration, position, and/or magnitude of the delivered thermal energy may be tailored to ablate tumor tissue within a desired region of the tumor while avoiding the delivery of damaging amounts of thermal energy to healthy tissue. The temperature information may be fed to the generator algorithm to determine the amount of power to provide to the first pole and the second pole The RF energy delivery probe 410 may be inserted into a vertebral body of the patient. If a single RF energy delivery probe 410 is used to access the vertebral body, this is called unipedicular access. A second RF energy delivery probe 410' may be used to access the vertebral body, this is called bipedicular access.

In some embodiments, the distal portion 412 of the RF energy delivery probe 410 may be articulated relative to the proximal portion of the RF energy delivery probe. In other words, the RF energy delivery probe 410 transitions from a linear configuration to a non-linear configuration.

FIGS. 9A-9C illustrate the RF energy delivery probe 410 in three different configurations. FIG. 9A illustrates the RF energy delivery probe 410 in a straight configuration. FIG. 9B illustrates the RF energy delivery probe 410 in an articulated configuration. FIG. 9C illustrates the RF energy delivery probe 410 in an hyperextended configuration. During an ablation procedure, the if the RF energy delivery probe 410 is articulated to reach the tumor (as illustrated in FIG. 9B), it may be desirable to return the RF energy delivery probe 410 to a straight configuration (as illustrated in FIG. 9A) in order to remove the RF energy delivery probe 410 through a sheath and out of the body. In some circumstances, when the RF energy delivery probe is articulated, the RF energy delivery probe 410 develops a positional memory that causes the RF energy delivery probe to not be entirely straight when returned to a straight configuration. This slight variation (due to memory effects of the materials of the device) at the distal portion 412 that is not straight can make it more difficult to remove the RF energy delivery probe 410. Accordingly, the RF energy delivery probe 410 may be configured such that the distal portion 412 thereof may be articulated back "past" the initial zero position to compensate for any memory effects in the materials. Thus, a user may hyperextend the RF energy delivery probe 410 slightly past the straight configuration (as illustrated in FIG. 9C) up to an angle 81, causing the RF energy delivery probe 410 to hyperextend past the longitudinal axis of the RF energy delivery probe 410. In some embodiments, the angle $\theta_1$ may extend up to 20° past the longitudinal axis of the RF energy delivery probe 410. In some embodiments, the angle $\theta_1$ may extend up to 10° past the longitudinal axis of the RF energy delivery probe 410. This hyperextension may counteract the positional memory of the articulation and facilitates the removal of the RF energy delivery probe 410. Angle $\theta_1$ is measured in the opposite direction as the angle at which the RF energy delivery probe 410 is configured for primary articulation. In other words, primary articulation (such as shown in FIG. 9B) would be measured in a first direction from a neutral axis of the RF energy delivery probe 410 while the ability to "hyperextend" refers to the ability of the RF energy delivery probe 410 to return back toward, and past, the neutral axis when returning from the primary articulated state.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

We claim:

1. A system for tumor ablation, the system comprising:
   a first probe comprising:
     a first conductor;
     a second conductor disposed distal to the first conductor;
     an insulator bushing disposed between the first conductor and the second conductor;
     a distal thermocouple to measure a temperature at a location on the second conductor;
     a plurality of thermocouples that are disposed between the first conductor and the second conductor; and
   a generator to produce a current to be conducted between the first conductor and the second conductor to create an ablation region;
   wherein the system is configured to create a symmetric ablation region.

2. The system for tumor ablation of claim 1, wherein the plurality of thermocouples are disposed proximal to the insulator bushing.

3. The system for tumor ablation of claim 1, wherein the plurality of thermocouples are evenly spaced.

4. The system for tumor ablation of claim 1, wherein the first probe further comprises a first insulator and a second insulator disposed radially between the first conductor and the second conductor, and wherein the plurality of thermocouples are disposed radially and longitudinally between the first insulator and the second insulator.

5. The system for tumor ablation of claim 1, wherein the plurality of thermocouples and the distal thermocouple are disposed on a flexible thermocouple circuit.

6. The system for tumor ablation of claim 5, wherein the flexible thermocouple circuit comprises at least two tails, wherein the plurality of thermocouples are disposed on a first tail and the distal thermocouple is disposed on a second tail, and wherein the second tail extends along the center of an inner diameter of the second conductor to a distal portion of the second conductor.

7. The system for tumor ablation of claim 1, wherein a distal portion of the first probe is configured to articulate relative to a proximal portion of the first probe.

8. The system for tumor ablation of claim 1, wherein the system further comprises a remote that manually controls the energy delivered to the first probe.

9. The system for tumor ablation of claim 1, wherein the system is configured to create a 1 cm symmetric ablation region.

10. The system for tumor ablation of claim 1, wherein the system is configured to create a 3.5 cm symmetric ablation region.

11. The system for tumor ablation of claim 1, wherein the generator further comprises a first port and a second port, wherein the first probe is configured to couple to the first port and a second probe is configured to couple to the second port.

12. The system for tumor ablation of claim 11, wherein the first port comprises a first indicia and the second port comprises a second indicia,
wherein the first probe comprises a third indicia and the second probe comprises a fourth indicia, and
wherein the first indicia corresponds with the indicia of the probe that is coupled to the first port and the second indicia corresponds with the indicia of the probe that is coupled to the second port.

13. An RF energy delivery probe for tumor ablation comprising:
a first tubular conductor;
a second tubular conductor partially disposed within the first tubular conductor and disposed such that a distal portion of the second conductor is distal to the first conductor;
an insulator bushing disposed between the first conductor and the second conductor; and
a distal thermocouple disposed at a distal end of the second tubular conductor to measure a temperature at the distal end of the probe;
a plurality of thermocouples disposed between the first tubular conductor and the second tubular conductor and proximal to the distal thermocouple,
wherein the RF energy delivery probe is configured to create an ablation region.

14. The RF energy delivery probe of claim 13, further comprising a first insulator and a second insulator disposed radially between the first conductor and the second conductor, and wherein the plurality of thermocouples are disposed between the first insulator and the second insulator.

15. The RF energy delivery probe of claim 13, wherein a distal portion of the RF energy delivery probe is configured to articulate relative to a proximal portion of the probe.

16. The RF energy delivery probe of claim 13, wherein the distal portion of the second tubular conductor is configured to extend and retract in the longitudinal direction of the RF energy delivery probe relative to the first tubular conductor.

17. The RF energy delivery probe of claim 13, wherein the plurality of thermocouples and the distal thermocouple are disposed on a flexible thermocouple circuit.

18. The system for tumor ablation of claim 17, wherein the flexible thermocouple circuit comprises at least two tails, wherein the plurality of thermocouples are disposed on a first tail and the distal thermocouple is disposed on a second tail, and wherein the second tail extends along the center of an inner diameter of the second tubular conductor to a distal portion of the second tubular conductor.

19. A method of ablating tumors in a patient, comprising:
inserting a first RF energy delivery probe within a patient to a tumor location, wherein the RF energy delivery probe comprises:
a first conductor,
a second conductor disposed distal to the first conductor; and
an insulator bushing disposed between the first conductor and the second conductor; and
a plurality of thermocouples that are disposed between the first conductor and the second conductor;
producing a current between the first conductor and the second conductor to create a symmetric ablation zone; and
measuring a temperature at a point on the second conductor.

* * * * *